US012767914B2

(12) United States Patent
Rao et al.

(10) Patent No.: US 12,767,914 B2
(45) Date of Patent: Oct. 20, 2026

(54) ADJUSTABLE FERMENTATION AND CELL CULTURE FLASKS WITH INTEGRATED ANALYTE SENSORS

(71) Applicant: University of Maryland, Baltimore County, Baltimore, MD (US)

(72) Inventors: Govind Rao, Ellicott City, MD (US); Yordan Kostov, Columbia, MD (US); Michael Tolosa, Columbia, MD (US); Xudong Ge, Woodstock, MD (US); Vikash Kumar, Catonsville, MD (US); Vida Rahmatnejad, Baltimore, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 1276 days.

(21) Appl. No.: 17/407,392

(22) Filed: Aug. 20, 2021

(65) Prior Publication Data

US 2021/0380915 A1 Dec. 9, 2021

Related U.S. Application Data

(63) Continuation-in-part of application No. PCT/US2020/017830, filed on Feb. 12, 2020.

(Continued)

(51) Int. Cl.
*C12M 1/24* (2006.01)
*C12M 1/00* (2006.01)

(Continued)

(52) U.S. Cl.
CPC ............ *C12M 23/08* (2013.01); *C12M 23/24* (2013.01); *C12M 23/26* (2013.01); *C12M 23/48* (2013.01);

(Continued)

(58) Field of Classification Search
CPC ...... C12M 23/08; C12M 23/24; C12M 23/26; C12M 23/48; C12M 41/26; C12M 41/32; C12M 41/34
See application file for complete search history.

(56) References Cited

U.S. PATENT DOCUMENTS 2,947,612 A 8/1960 DeLong
4,413,800 A * 11/1983 Kelson ................ B65B 67/1205 248/99

(Continued)

FOREIGN PATENT DOCUMENTS

CN 102787072 11/2012
CN 202773492 U 3/2013
CN 109022281 A 12/2018

OTHER PUBLICATIONS

Extended European Search Report for EP23186296.2. Mailed Jun. 11, 2023. 6 pages.

(Continued)

*Primary Examiner* — William H. Beisner
*Assistant Examiner* — Danielle B Henkel
(74) *Attorney, Agent, or Firm* — Casimir Jones, S.C.; Tristan A. Fuierer

(57) ABSTRACT

The present invention relates to collapsible and/or foldable fermentation and/or culture vessels fabricated of an adjustable frame including sections of gas permeable material or in the alternative a non-rigid gas permeable polymeric container or bag fabricated of either a gas permeable or non-gas permeable material with the further benefit of more efficient inventory space and disposal space, wherein the gas permeable material or non-gas permeable material comprises an analyte or pH sensing material integrated or impregnated into at least one section of the material.

9 Claims, 20 Drawing Sheets

Related U.S. Application Data

(60) Provisional application No. 62/809,796, filed on Feb. 25, 2019.

(51) Int. Cl.
*C12M 1/04* (2006.01)
*C12M 1/34* (2006.01)
*C12M 3/00* (2006.01)

(52) U.S. Cl.
CPC ............ *C12M 41/26* (2013.01); *C12M 41/32* (2013.01); *C12M 41/34* (2013.01)

(56) References Cited

U.S. PATENT DOCUMENTS

| | | | |
|---|---|---|---|
| 4,867,576 | A | 9/1989 | Boyd |
| 4,939,151 | A | 7/1990 | Bacehowski et al. |
| 5,047,347 | A | 9/1991 | Cline |
| 5,083,678 | A | 1/1992 | Waring |
| 5,174,458 | A | 12/1992 | Segati |
| 5,358,872 | A | 10/1994 | Mussi et al. |
| 5,391,496 | A | 2/1995 | Kayal et al. |
| 6,461,853 | B1 * | 10/2002 | Zhu ........................ C12M 23/14 435/243 |
| 6,520,457 | B1 * | 2/2003 | Yardley ............... B65B 67/1233 248/97 |
| 6,673,598 | B1 | 1/2004 | Akers et al. |
| D671,013 | S | 11/2012 | Fritsch |
| 8,945,917 | B2 | 2/2015 | Sarkar et al. |
| 9,440,789 | B2 * | 9/2016 | Moayed Sabeti ....... B65B 67/04 |
| 9,919,839 | B2 | 3/2018 | Mirvach |
| 2003/0008389 | A1 | 1/2003 | Carli |
| 2005/0148068 | A1 | 7/2005 | Lacey et al. |
| 2005/0239199 | A1 * | 10/2005 | Kunas ..................... B01F 35/51 435/297.1 |
| 2006/0182372 | A1 * | 8/2006 | Fadal, II .............. A45C 7/0077 383/80 |
| 2007/0178589 | A1 | 8/2007 | Wilson |
| 2007/0224676 | A1 | 9/2007 | Haq |
| 2007/0254356 | A1 | 11/2007 | Wilson et al. |
| 2008/0056625 | A1 | 3/2008 | Stanton |
| 2010/0130957 | A1 | 5/2010 | Smisson |
| 2011/0212519 | A1 | 9/2011 | Wilson et al. |
| 2013/0193164 | A1 | 8/2013 | Tom et al. |
| 2015/0125930 | A1 | 5/2015 | Gebauer et al. |
| 2018/0142200 | A1 | 5/2018 | Mason et al. |

OTHER PUBLICATIONS

Giambernardi, et al., 1997 Use of oxygen-permeable silicone rubber pouches for growing mass cultures of bacteria; *Letters in Applied Microbiology* 24; 207-210.
Falch, et al. 1963, Diposable Skaker Flasks, *Biotechnolgy and Bioengineering*, V.V, 211-220.
Extended European Search Report for PCT/US2020017830. Mailed Nov. 21, 2022. 5 pages.

* cited by examiner

Ru dye

ADJUSTABLE FERMENTATION AND CELL CULTURE FLASKS WITH INTEGRATED ANALYTE SENSORS

CROSS REFERENCE TO RELATED APPLICATION

This application is a Continuation-in-Part application claiming priority to co-pending PCT Application NO. PCT/US2020/017830 filed on Feb. 12, 2020, which in turn claims priority to U.S. Provisional Patent Application No. 62/809,796 filed on Feb. 25, 2019, the contents of which are hereby incorporated by reference herein for all purposes.

TECHNICAL FIELD

The present invention relates to collapsible and/or foldable fermentation and/or culture vessels fabricated of gas permeable or non-gas permeable material and may include an adjustable frame further including sections of gas permeable material or in the alternative a non-rigid gas permeable polymeric container or bag fabricated of a gas permeable material for gas exchange with the further benefit of more efficient inventory space, disposal space and can be used as alternatives or replacement of rigid-wall containers, such as those made of glass, metal or a rigid polymer.

BACKGROUND OF THE INVENTION

Related Art

The culture of cells is a critical element of biotechnology. Cells are cultured in small quantities during the research stage, and typically the magnitude of the culture increases as the research moves towards its objective of benefiting human and animal health care. The culture or processing of cells typically requires the use of a device to hold the cells, for example in an appropriate culture medium when culturing the cells. Certain devices and methods have become well established for research stage cell culture because they allow a wide variety of cell types to be cultured and are therefore useful to the widest audience. The known devices include shaker flasks, roller bottles, T-flasks, and bags. Such devices are widely used but suffer from several drawbacks, including the material they are made of, such as glass, metal, or hard plastic vessels. Such vessels are expensive and require maintenance, as they are not disposable or sterile. In order to maintain a sterile or aseptic environment for cell culture, the vessels require sterilization, usually by autoclave. Therefore, the cell culture vessels must be washed and sterilized prior to and/or subsequent to their use. In addition, because glass and hard plastic cell culture vessels are not usually disposable, it is necessary to have adequate space for storage of such vessels. Thus, as glass, metal, and hard plastic cell culture vessels are expensive, not disposable, and require extensive maintenance, there is a need for cell culture vessels that are inexpensive, disposable, collapsible, and pre-sterilized.

SUMMARY OF THE INVENTION

The present invention provides for different embodiments of collapsible or foldable vessels fabricated of a semi-rigid material and providing a frame for a fluid reservoir.

In one aspect, the present invention provides for a conical shaped flask comprising:

a. a conical shaped frame comprised of two rigid rod-type supports each having proximal end forming a flat base and two opposing upwardly extending distal ends to form a generally conical body, wherein the flat bases of the two rigid supports are connected at a central pivot point thereby allowing the two rigid rod-type supports to form a conical body portion when separated furthest from each other and foldable into an essentially flat frame when adjacent;

b. a rigid circular ring cap forming a tubular neck for placement and connecting thereto the upwardly extending distal ends to stabilize the conical shaped frame, wherein the rigid circular ring cap has an exterior and interior edge; and c. a non-rigid gas permeable polymeric container or bag fabricated of a gas permeable polymeric material and sized to fit within the conical body portion and attached to the interior edge of the circular ring cap for positioning therein.

Notably, the rigid circular ring cap preferably comprises four recesses/slots equally distributed within the bottom of the circular ring cap for insertion and stabilization of the upwardly extending distal ends. Further, the two rigid rod-type supports preferably have hook type attachments for securing the non-rigid gas permeable polymeric container or bag to the conical body portion, thereby providing the full extent of the fluid capacity of the polymeric container or bag. The rigid circular ring cap may further comprise a top stopper or a rigid screw type cap for closure of the non-rigid gas permeable polymeric container or bag. Further, the circular ring cap can be fabricated as a cylindrical ring to form a neck wherein the neck has a uniform internal diameter for its entire height. The height of the neck can be from about ½" to about 2". The interior diameter of the rigid circular ring cap is of a sufficient size for ease of transfer of fluids into and out of the polymeric bag. Additionally, this rigid ring can be threaded to provide for a screw on top to ensure closure of the flask.

The non-rigid gas permeable polymeric container or bag fabricated of a gas permeable polymeric material may further comprise at least one analyte sensing material or pH sensing material integrated into the gas permeable polymeric material, either as impregnation within the polymer or microencapsulated, for determining the presence of such analyte as oxygen, nitrogen, glucose, carbon dioxide, ammonia and other gases or components. A sensing material may also be included in the polymeric material to determine the pH of the solution within the container or bag.

In yet another aspect, the present invention relates to a T-flask that provides the advantages of being disposable, collapsible, and pre-sterilized.

A T-flask of the present invention comprises:

a. four rectangular frames each comprising four rigid support members pivotably attached to each other by corner hinges to form a two dimensional rectangular shape, wherein the four rigid support members are fabricated of a rigid material or substantially rigid material such as a polymer, metal or the like, wherein the four rectangular frames are connected through the corner hinges and pivot with respect to each other to an expanded configuration to form a three dimensional rectangular structure and a collapsed configuration wherein the rectangular frames lie approximately parallel to each other, wherein the hinges include locking mechanism to support the frame in expanded configuration; and b. a non-rigid gas permeable polymeric container or bag comprising a chamber, a neck connected to the chamber for introducing fluids into the chamber, a closure cap attachable to the neck, wherein the chamber is sized to fit within the three dimensional rectangular structure, wherein the chamber of the non-rigid gas permeable polymeric container or bag is communicatively connected to the four rectangular frames, and wherein the neck and closure cap are not positioned within the rectangular frame.

Again, the non-rigid gas permeable polymeric container or bag fabricated of a gas permeable polymeric material may further comprise at least one analyte sensing material or pH sensing material integrated into the gas permeable polymeric material, either as impregnation of the polymer or microencapsulated, for determining the presence of such analyte as oxygen, nitrogen, glucose, carbon dioxide, ammonia, and other gases or components. A sensing material may also be included in the polymeric material to determine the pH of the solution within the container or bag.

In a further aspect, the present invention a collapsible flask comprising:

an Erlenmeyer flask shaped vessel fabricated of a gas permeable polymeric film comprising: a flat base, a generally conical body portion, a generally tubular neck having a diameter less than the body portion, wherein the tubular neck comprises an opening for moving fluid into and out of the vessel, wherein gas permeable polymeric film is sufficiently strong to maintain shape of the vessel and sufficiently flexible to allow collapsibility of the vessel. Optionally the tubular neck of the vessel may be provided with a rigid sealable cap and the tubular neck can include a threaded area for a screw on cap.

The collapsibility of the vessel is easy effected by collapsing the top section into the middle section and both of same into the bottom section of the vessel when the vessel is in an upright position. Thus, the sections of the vessel are collapsed along a vertical plane to form a lateral configuration. In the compressed or collapsed position, the vessel is in a better arrangement for storage or transport. The vessel can easily be opened into an expanded vessel by simply moving the top and middle section away from the bottom section.

The gas permeable polymeric film provides adequate rates of carbon dioxide and oxygen permeability while preventing passage of liquid. Several gas-permeable materials have gas permeability sufficient to permit free passage of oxygen and carbon dioxide and can be selected from a group including, but not limited to, silicone, fluoroethylenepolypropylene, polyolefin, polyethylene, ethylene vinyl acetate copolymer, a cellulose acetate, a methacrylate, a phthalate, or a hybrid material such as the combination of nylon and silicone. Hybrid materials are formed by two or more components and combine the intrinsic characteristics of its individual constituents to additional properties due to synergistic effects between the components. Thus, the properties of hybrid nanomaterials can be tuned by changing their composition and morphology, leading to materials with enhanced performance characteristics, such as high thermal stability, mechanical strength, light emission, gas permeability, electron conductivity, and controlled wetting features.

The collapsible Erlenmeyer flask shaped vessel fabricated of a gas permeable polymeric film may further comprise at least one analyte sensing material or pH sensing material integrated into the gas permeable polymeric material, either as impregnation of the polymer or microencapsulated, for determining the presence of such analyte as oxygen, nitrogen, glucose, carbon dioxide, chloride, and other gases or components. A pH sensing material may also be included in the polymeric material to determine the pH of the solution within the container or bag.

In another aspect, the present invention provides a collapsible flask comprising:

an Erlenmeyer flask shaped vessel fabricated of both a gas permeable and a non-gas permeable polymeric film comprising: a flat base, a generally conical body portion, a generally tubular neck having a diameter less than the body portion and a mouth of the tubular neck for moving fluid into and out of the vessel, wherein the generally conical body portion comprises strips of connecting gas permeable and non-gas permeable polymeric sections, wherein the non-gas permeable sections provide sufficient support for maintaining the conical shape and the gas permeable polymeric sections cover a greater area from that of the non-gas permeable polymeric sections. Both the gas permeable and non-gas permeable polymeric films are sufficiently strong to maintain shape of the vessel and sufficiently flexible to allow collapsibility of the vessel. Optionally the tubular neck and mouth of the vessel may be provided with a rigid sealable cap, wherein the tubular neck can include a threaded section to provide closure with a screw on cap.

The collapsibility of the vessel is easy effected by collapsing the top section into the middle section and both in the bottom section of the vessel when the vessel is in an upright position. Thus, the sections of the vessel are collapsed vertically to form a compressed configuration. In the compressed or collapsed position, the vessel is in a better arrangement for storage or transport. The vessel can easily be compressed and opened into an expanded vessel by simply moving the top, and middle section away from the bottom section.

The gas permeable polymeric film provides adequate rates of carbon dioxide and oxygen permeability while preventing passage of liquid. Several gas-permeable materials have gas permeability sufficient to permit free passage of oxygen and carbon dioxide and can be selected from a group including, but not limited to, silicone, fluoroethylenepolypropylene, polyolefin, ethylene vinyl acetate copolymer, a cellulose acetate, a methacrylate, a hybrid material, or a phthalate. The non-gas permeable sections can be any plastic commonly used in traditional culture vessels, or any other cell attachment material known to those skilled in the art.

The gas permeable polymeric material and non-gas permeable material may further comprise at least one analyte sensing material integrated into the gas permeable polymeric material, either as impregnation of the polymer or microencapsulated, for determining the presence of such analyte as oxygen, nitrogen, glucose, carbon dioxide, ammonia, chloride, and other gases or components. A sensing material may also be included in the polymeric material to determine the pH of the solution within the container or bag.

In a still further aspect, the present invention provides for an inflatable flask structure comprising:

i) a plurality of pneumatically interconnected, elongate inflatable tubes positioned in spaced-apart relation to provide a conical shaped structure for being inflated in unison, said tubes defining a flask type structure have an opening at the proximal end and flat bottom structure at the distal end;

ii) valve means for inflating the tubes; and iii) optionally a plurality of wall panels attached from and between adjacent tubes to define an enclosure of the flask, wherein the plurality of wall panels is fabricated from a gas permeable polymeric material and wherein the inflatable tubes are fabricated from an impermeable and flexible polymeric material.

The inflatable tubes are preferably fabricated of a flexible gas impermeable material such as a rubberized material, polymeric material, or a thermoplastic sheet material, wherein the material has sufficient density to resist passage of air under pressure. When inflated the flask sharped structure is formed. Valve means are provided for inflating the tubes, wherein the valve means includes a manifold into which all of the tubes interconnect and the tubes are connected with an air pump and the tubes.

To provide a supporting system for the above inventive structures, the present invention further provides for an inflatable holder for supporting a flask comprising:

a flexible bag body having an open end wherein the open end comprises an adjustable valve for introducing compressed air into the flexible bag, wherein the adjustable valve is sealable to retain the compressed air after inflating, wherein the bag is sized sufficiently for providing an inflatable extendible rim to encompass and provide support for an inserted flask.

In another aspect, the present invention provides for a collapsible conical shaped Erlenmeyer flask comprising three sections, wherein the first section is a non-flexible neck section, the second section comprises a non-flexible flat bottom bowl section and a third section comprising a flexible sleeve that is positioned between the first and second section and connected to each to form a sealed collapsible Erlenmeyer flask, wherein the flexible sleeve collapsible folds upon itself to position the non-flexible neck section closer to the non-flexible flat bottom bowl section. Importantly, the flexible sleeve is fabricated of a gas permeable membrane, as described herein below and preferably a silicone material. In the folding process, the neck section and substantially all of the flexible sleeves are contained with the non-flexible flat bottom bowl section, thereby reducing the size for easy storage.

The flexible sleeve comprises a first opening having smaller cross-section diameter than a second opening, wherein the first and second opening are positioned at opposite ends of the flexible sleeve and where in the first opening is connect to the non-flexible neck section and the second opening is connect to the non-flexible flat bottom bowl section. The flexible sleeve is connected to both the non-flexible neck section and the non-flexible flat bottom bowl section by meeting the edges of each and overlapping a bottom section of the non-flexible neck section and the top section of the non-flexible flat bottom bowl section. The flexible sleeve has the ability and elasticity to stretch over the bottom edge of the neck section and the top edge of the non-flexible flat bottom bowl section. Additionally, a sealing band can be connected to flexible sleeve at the junction point of the overlapping sleeve section to the neck section and flat bottom bowl section. The sealing bands may be a narrow metal strip, wherein the bands can be slipped over the neck section for positioning at the appropriate junction points. The non-flexible neck section can include a threaded section to provide the option of a screwable cap for closure of the flask.

The flexible sleeve is fabricated from a gas permeable silicone type material. Silicone films may be less than about 3 mm, about 2 mm, about 1 mm, or about 0.8 mm in the surface areas where gas transfer is desired. The best selection of material and thickness depends on the application, however, preferably silicone rubber has been found to be most effective for bacteria growth because bacteria grown in the silicone rubber pouches or bags can readily take up oxygen and release waste gases, such as carbon dioxide. Notably, silicone rubbers are elastomers based on high molecular weight linear polymers, generally polydimethysiloxanes, which also may be modified with functional groups.

The flexible sleeve material may further comprise at least one analyte sensing material integrated into the gas permeable polymeric material or non-gas permeable material, either as impregnation of the polymer or microencapsulated, for determining the presence of such analyte as oxygen, nitrogen, glucose, carbon dioxide, ammonia, chlorine and other gases or components. A sensing material may also be included in the polymeric material to determine the pH of the solution within the container or bag.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings

BRIEF DESCRIPTION OF THE FIGURES

FIG. 1 B illustrates an example of a collapsible bag in expanded configuration, according to one embodiment of the invention.

FIG. 2 B illustrates rigid cap of FIG. 2 A connected to the support frame of FIG. 1 A.

FIG. 3 B illustrates the frame support of FIG. 1 A in a foldable position.

FIG. 6 B illustrates the support frame of FIG. 6 a collapsed into a folded frame.

FIG. 8 B illustrates the flask of FIG. 8 A in a collapsed configuration.

FIG. 9 B illustrates the flask of FIG. 9 A in a collapsed configuration.

FIG. 11 B illustrates an inflatable flask with inflatable tubes forming a conical structure.

FIG. 11 C illustrates the inflatable flask of FIG. 11A in a collapsed form.

DETAILED DISCLOSURE OF THE INVENTION

Figure 1B:
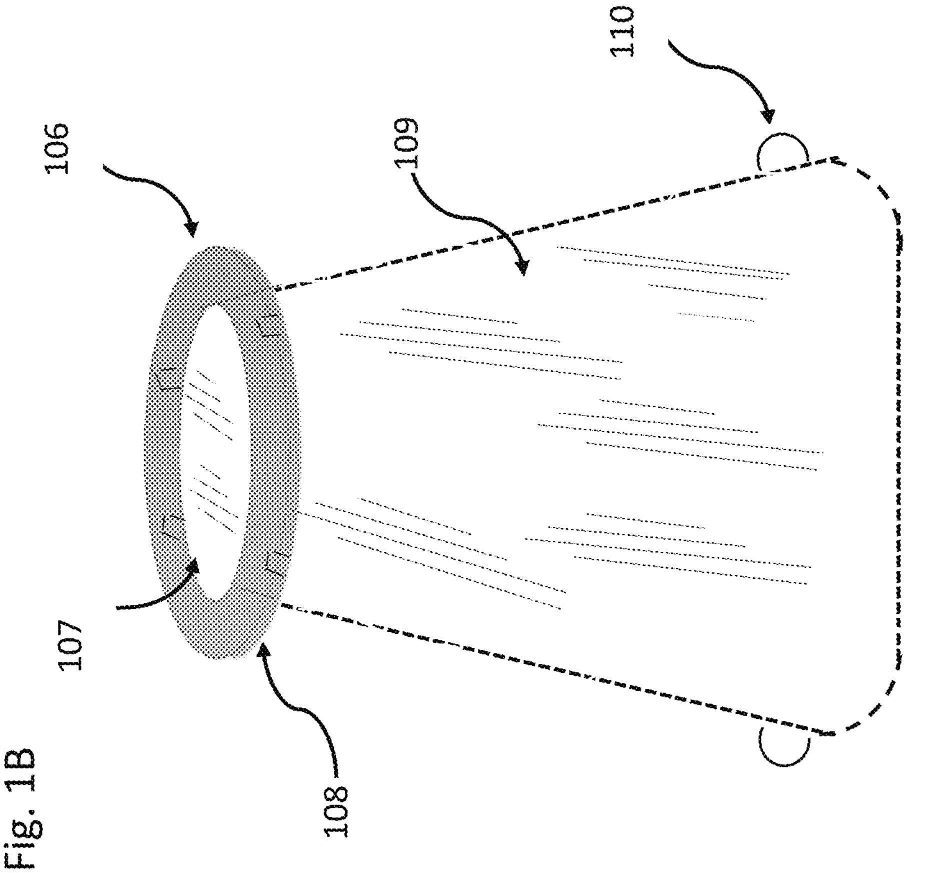
FIG. 1 A illustrates a foldable support frame in an expanded configuration according to one embodiment of the invention.

Various embodiments of the disclosure will be described in detail with reference to drawings. Reference to various embodiments does not limit the scope of the invention. Additionally, any examples set forth in this specification are not limiting and merely set forth some of the many possible embodiments of the claimed invention. Like numbers used in the figures refer to like components, steps, and the like.

All scientific and technical terms used herein have meanings commonly used in the art unless otherwise specified. The definitions provided herein are to facilitate understanding of certain terms used frequently herein and are not meant to limit the scope of the present disclosure.

"Include," "includes," or like terms means encompassing but not limited to, that is, inclusive and not exclusive.

"Integrated" means wherein the analyte is dissolved, distributed, dispersed and/or impregnated into at least a section of the polymeric material.

"Optional" or "optionally" means that the subsequently described step, feature, condition, characteristic, or structure, occurs/is present or does not occur/is not present, while still being within the scope described.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

The vessels or flasks, the methods of making the vessels or flasks, and the method of using the vessels or flasks, described herein may include components or steps described herein, plus other components or steps not described herein.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "has", "having", "include", "includes", "including", "comprise", "comprises", "comprising" or the like are used in their open-ended inclusive sense, and generally mean "include, but not limited to", "includes, but not limited to", or "including, but not limited to".

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations. Directional descriptors used herein with regard to cell culture vessels often refer to directions when the vessel is oriented for purposes of culturing cells in the apparatus.

While various features, elements or steps of particular embodiments may be disclosed using the transitional phrase "comprising," it is to be understood that alternative embodiments, including those that may be described using the transitional phrases "consisting of" or "consisting essentially of" are implied.

The present invention provides for different embodiments of culture vessels or flasks that provide for gas permeability and structural integrity while also providing for vessels or flasks that are foldable and collapsible to provide for space-conscious vessels that are when stored occupy considerably less space than traditional rigid vessels or flasks. Some embodiments include at least a collapsible polymeric gas permeable container or bag and may differ depending upon the intended use but may have up to or greater than a 5 Liter capacity in some embodiments, or as small as 25 mL capacity or even smaller in other embodiments. Various example vessels or flasks may further include additional support members to contact and support the non-rigid gas permeable polymeric container or bag when in expanded configuration.

According to one embodiment, the non-rigid polymeric containers or bags are collapsible to lie substantially flat, or at least to a reduced profile, and expandable to define a volume when in use. The non-rigid gas permeable polymeric containers or bags may be constructed from flexible, non-rigid materials, having an open end and a closed end. The non-rigid gas permeable polymeric containers or bags may be foldable or otherwise collapsible for storage. The non-rigid gas permeable polymeric containers or bags may be constructed in any suitable configuration that would define the desired shape and volume when expanded for use.

For example, according to one embodiment, a non-rigid gas permeable polymeric container or bag may be formed as a single sheet using thermal forming techniques or blow molding techniques. According to another embodiment, however, the non-rigid gas permeable polymeric container or bag may be formed from two sheets (having any pre-formed shape) mated together at or near the edges, using any suitable mating technique, such as, but not limited to, solvent welding, radio frequency ("RF") welding, sonic welding, heat sealing, adhesives, and the like. The open end of the non-rigid gas permeable polymeric container or bag may be permanently or removably sealed to the underneath side of the rigid cap, or may be sealed to the outer edge of the rigid cap. According to one embodiment, the closed end of the container or bag can be formed in several different shapes to ensure that the fluid contained within the container or bag does not pool or gather along the bottom.

Examples of collapsible containers or bags may include a rigid cap to which the non-rigid gas permeable polymeric container or bag is attached. The rigid cap assists in defining the open space and cross-sectional geometry of the container by defining the shape of the open end. The geometry of the rigid cap may vary, according to various embodiments described herein. For example, in one embodiment the rigid cap may have a substantially circular geometry, whereas in other embodiments the rigid cap may be more elongated, ovular, or elliptical in shape. In yet another embodiment, the rigid cap may be formed as a long, narrow cap, having a reduced width that is just wide enough to house one or more ports.

Any number of fittings may be used to provide a fluid inlet, vent, or vacuum port, such as, but not limited to, barbed fitting female/male luer loc fitting, straight fitting, relief valve, one-way valve, and the like. The selection of the fitting will depend upon the intended use of the port. For example, a relief valve or one-way positive check valve may be used as a venting port, whereas a barbed fitting or female luer loc fitting may be used as an inlet port. According to one embodiment, the rigid cap may also have one or more fluid filters for filtering debris and other materials from the fluid flowing therethrough.

In some example embodiments, additional support members may also be included to support the non-rigid gas permeable polymeric container or bag when in expanded configuration. For example, the support members may be affixed to multiple points on the exterior surface of the non-rigid gas permeable polymeric container or bag, such that when the support members are expanded, they positively expand the non-rigid gas permeable polymeric container or bag to assist in defining the form, shape, and rigidity of the container or bag during use. These support members may be collapsible or otherwise deconstructed to also lie in a substantially flat configuration, or have a reduced profile, when not in use. In another example, the support members may be one or more adjustable support arms that are attachable to the rigid cap providing a tension to expand the non-rigid gas permeable polymeric container or bag in a direction away from the rigid cap. Any other suitable configuration of rigid support members that are collapsible and expandable to support the non-rigid gas permeable polymeric container or bag may be used with any of the example embodiments of collapsible fluid vessels or flasks described herein.

In some versions, the non-rigid gas permeable polymeric container or bag can be affixed to the support frame in a manner, such as by loops, clips, etc., as described more fully below, to resist the forces created by negative pressure which may otherwise cause the container to separate from the support frame and collapse inward.

The non-gas permeable polymeric material for supporting the described vessel or flasks is formed of any suitable material. Preferably, materials intended to contact cells or culture media are compatible with the cells and the media. Typically, cell culture components are formed from polymeric material. Examples of suitable polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

Cell culture containers or bags that are constructed with gas permeable films advantageously provide a large surface area for gas exchange while maintaining a closed system. Disposables bags also helps reduce the risk of contamination for the cell culture and for the environment. Gas permeable films should be selected based on a variety of characteristics including gas permeability, moisture vapor transmission, capacity to be altered for desired cell interaction with cells, optical clarity, physical strength, and the like. A wide variety of information exists that describe the types of gas permeable materials that have been successfully used for cell culture.

Silicone films, made of silicone rubber, and used for cell culture bags have high oxygen and carbon dioxide permeability, good optical clarity, good resistance to puncture, typically do not bind cells, and can be easily fabricated into a wide variety of shapes. Silicone films may be less than about 3 mm, about 2 mm, about 1 mm, or about 0.8 mm in the surface areas where gas transfer is desired. The best selection of material and thickness depends on the application, however, preferably silicone rubber has been found to be most effective for bacteria growth because bacteria grown in the silicone rubber pouches or bags can readily take up oxygen and release waste gases, such as carbon dioxide. Notably, silicone rubbers are elastomers based on high molecular weight linear polymers, generally polydimethysiloxanes, which also may be modified with functional groups.

Fluoropolymer films have desirable characteristics that make them a popular choice for culture bags. Fluoropolymer films are considered biologically, chemically, and immunologically inert, as well as being hydrophobic. Further, fluoropolymer films like FEP (fluorinated ethylene-propylene) do not trigger immune responses in immune cells and progenitor immune cells. Preferred fluoropolymer films include fluorinated ethylene-propylene (FEP), polytetrafluoroethylene (PTFE), 3M™ Dyneon™ TFM™ modified PTFE, polyvinylidenefluoride (PVDF), tetrafluoroethylene-perfluoro(propyl vinyl ether) (PFA), polyvinylidene difluoride (PVF), polychlorotrifluoroethlylene (PCTFE), tetrafluoroethylene/hexafluoropropylene/ethylene copolymer (HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers (TFE/P), tetrafluoroethylene/hexafluoropropylene copolymers (FEP/HFP), hexafluoropropylene/tetrafluoroethylene/vinylidene copolymer (THV), or perfluoro(1-butenyl vinyl ether) homocyclopolymer having functionalized polymer-end groups.

The gas permeable polymeric material and/or non-gas permeable material may further comprise at least one analyte sensing material integrated into the gas permeable polymeric material, either as impregnation of the polymer or microencapsulated, for determining the presence of such components as oxygen, nitrogen, glucose, carbon dioxide, chloride, and other gases or components. A sensing material may also be included in the polymeric material to determine the pH of the solution within the container or bag.

Sensing materials may include luminescent, chemiluminescent, phosphorescent, and fluorescent detector compounds that exhibit strong luminescence upon irradiation, wherein measuring the change in intensity, lifetime, anisotropy, or any other measurable parameter determines the level within the container. Examples of suitable chemiluminescence detector molecules include but without limitation, peroxidase, bacterial luciferase, firefly luciferase, functionalized iron-porphyrin derivatives, luminal, isoluminol, acridinium esters, sulfonamide, and others.

Compounds that are effective for measuring oxygen may include ruthenium-based molecules or metallo-porphyrin-type molecules. Other, less commonly used, oxygen-sensitive compounds include fluorescein compounds, polycyclic aromatic hydrocarbons, and other organic compounds. containing compounds. Glucose sensing may include glucose sensitive boronic acid containing fluorophores as described in U.S. Pat. No. 7,718,804, the content of which are incorporated herein. Additionally, acrylodan and ruthenium bis-(2,2'-bipyridyl)-1,10-phenanthroline-9-isothiocyanate may be used for glucose testing and/or glutamine. A well-known fluorescent dye, that being 8-hydroxy-1,3,6-pyrene trisulfonic acid (HPTS) may be used for a pH indicator. Others may include fluorescein, Vita Blue, and Eosin. An energy-transfer fluorosensor for detection of carbon dioxide ($CO_2$) may include dyes such as m-cresol purple, sulforhodamine 101, fluorescein, etc. Ammonia detection may be detected with a dye such as ninhydrin to yield a purple coloration. Chlorine gas may be determined by the use of o-tolidine, 3,3',5,5'-tetramethylbenzidine and dithizone noting a color change when reacting with Chlorine.

Excitation light sources may include arc lamps and lasers, natural sunlight, laser diodes and light emitting diode source, and both single and multiple photon excitation sources. The detector used in the detection system needs to be compatible with the emission spectrum of the energy emitting compound and the measurement method (i.e., intensity or lifetime), and a 2-D array of detectors can be used to image a spatial gradient in oxygen. Simple point detectors such as photodiodes and photomultiplier tubes (PMTs) are often used for emission detection in oxygen sensors due to their simplicity and fast response time.

The sensors are preferably integrated or impregnated into the polymeric material by methods known in the art. For example, the polymeric material is soaked in the analyte sensing component for inclusion into the polymeric material. For example, the impregnation of the film with a sensor can be achieved by dissolving both a polymer film and the sensor in a common volatile solvent, followed by casting on a leveled surface to allow the solvent to evaporate, thus forming a polymer film containing an impregnated sensor.

Turning now to a discussion of the drawings, the collapsible reservoir may be further understood with reference to FIGS. 1-20, providing examples of non-limiting embodiments.

Figure 1A:
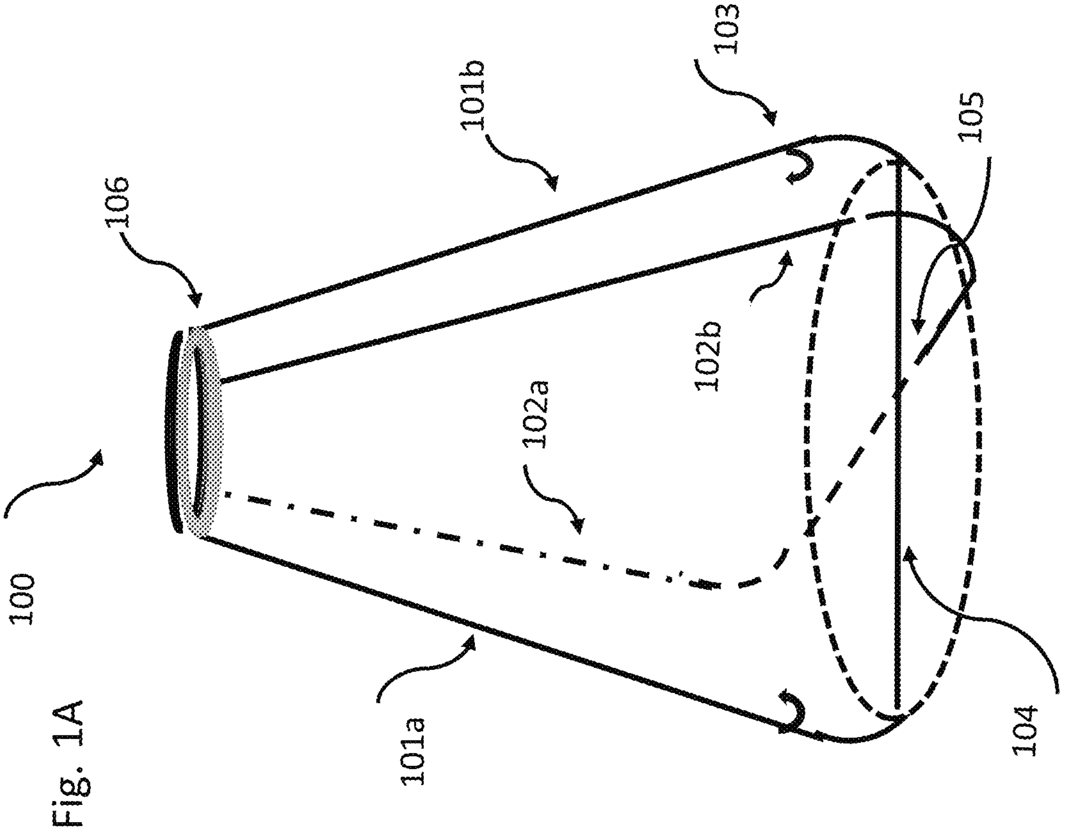

FIG. 1A illustrates a conical support frame 100 in an expanded configuration which includes two rigid rod-type supports 101 and 102 each having proximal end forming a flat base and two opposing upwardly extending distal ends 101*a* and 101*b* and 102*a* and 102*b* to form a generally conical body, wherein the flat base 104 of the two rigid supports are connected at a central pivot point 105 thereby allowing the two rigid rod-type supports to form a conical body portion when separated furthest from each other. The conical support frame 100 further comprises a rigid circular ring cap 106 forming a tubular neck for placement and connecting thereto the upwardly extending distal ends 101*a* and 101*b* and 102*a* and 102*b* to stabilize the conical shaped frame. The conical support frame 100 and circular cap 106 may be made from any rigid or substantially rigid polymeric materials described herein or otherwise suitable for such purposes, such as polyethylene (high-density or low-density polyethylene HDPE or LDPE), polyvinylchloride (PVC), polypropylene (PP), polystyrene (PS) including high impact polystyrene, polyamides (PA), acrylonitrile butadiene styrene (ABS), polycarbonate (PC), polycarbonate/acrylonitrile butadiene styrene (PC/ABS) etc. The upwardly extending distal ends 101*a* and 101*b* and 102*a* and 102*b* of the rigid rod can be configured in shapes including circular, triangular, rectangular, and cubic. Notably, the outside corners of the frame are curved. Such curved corners provide for easy fitting into flask clamp system and platform that are commercially available to hold Erlenmeyer flask and provide stabilization during any shaking of the flask.

FIG. 1B illustrates the rigid circular ring cap 106 having an exterior edge 108 and interior 107 edge; and a non-rigid gas permeable polymeric bag 109 fabricated of a gas permeable polymeric material and sized to fit within the conical body portion and attached to the interior edge 107 of the circular ring cap for positioning therein. The gas permeable polymeric bag is shown extended but is collapsible when inserting into the conical support frame 100. Optionally the gas permeable polymeric bag can include ring type attachments 110 that can be connect to hooks 103 on the support frame 100 to extend the gas permeable bag when in the conical support frame 100. Preferably the gas permeable polymeric bag is fabricated from a material that permits free passage of oxygen and carbon dioxide and can be selected from a group including, but not limited to, a silicone compounds such as polydimethylsiloxane (PDMS), poly1-trimethylsilyl-1-propyne (PMSP), polypropylmethylsiloxane, polytrifluoropropylmethylsiloxane, and polyphenylmethylsiloxane; fluoroethylenepolypropylene, polyolefin, ethylene vinyl acetate copolymer, polyethylene, a cellulose acetate, a methacrylate, a hybrid material or a phthalate. Preferably, a silicone compound is used to fabricate the pouch.

Figure 2B:
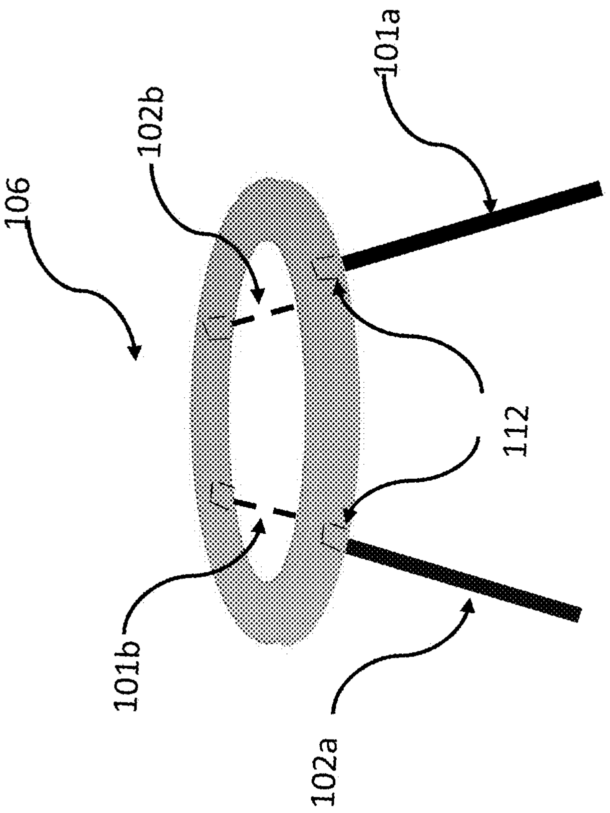
FIG. 2 A illustrates an example of a rigid cap, according to one embodiment of the invention.
Figure 2A:
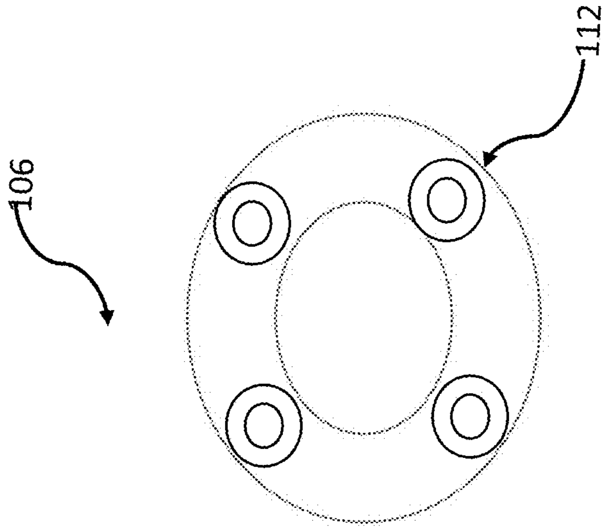

FIG. 2 A illustrates the rigid circular ring cap 106 with four equally separated recesses 112 that hold and provide support for the upwardly extending distal ends 101*a* and 101*b* and 102*a* and 102*b* to stabilize the conical shaped frame. The rigid circular ring cap 106 has sufficient size such as depth of material to include the recesses so the recesses are deep enough to hold the distal ends 101*a* and 101*b* and 102*a* which can be constructed with a click in or locking connection. FIG. 2 B shows the upwardly extending distal ends 101*a* and 101*b* and 102*a* locked in the recesses 112 of the rigid circular ring cap.

Figure 3B:
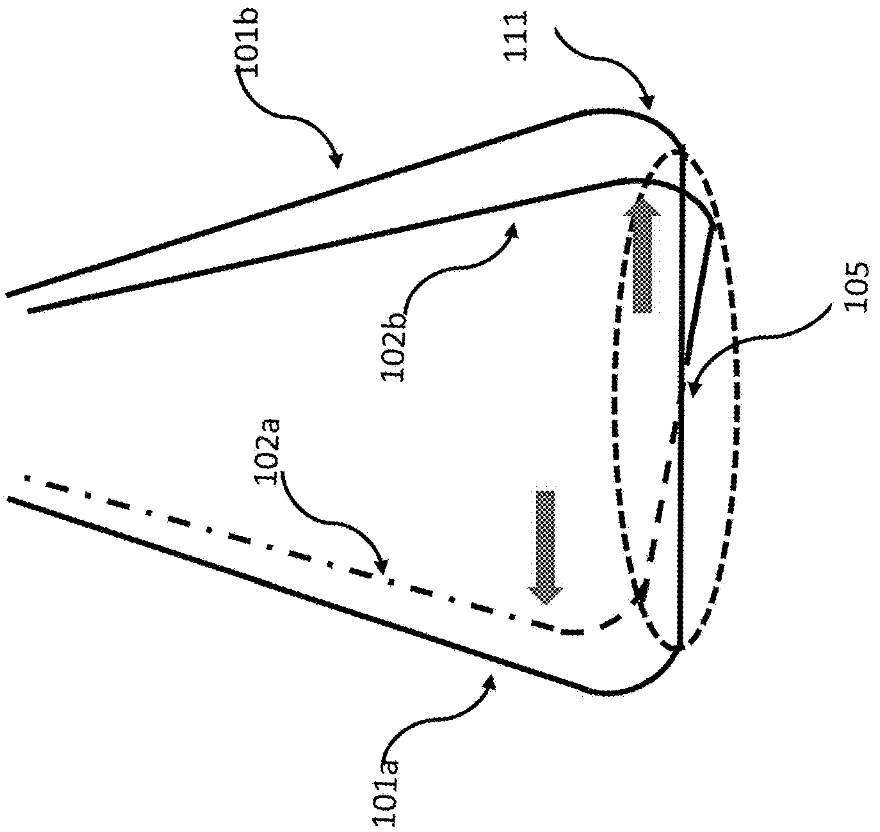
FIG. 3 A illustrates the frame support of FIG. 1 A and the collapsible bag of FIG. 1B.
Figure 3A:
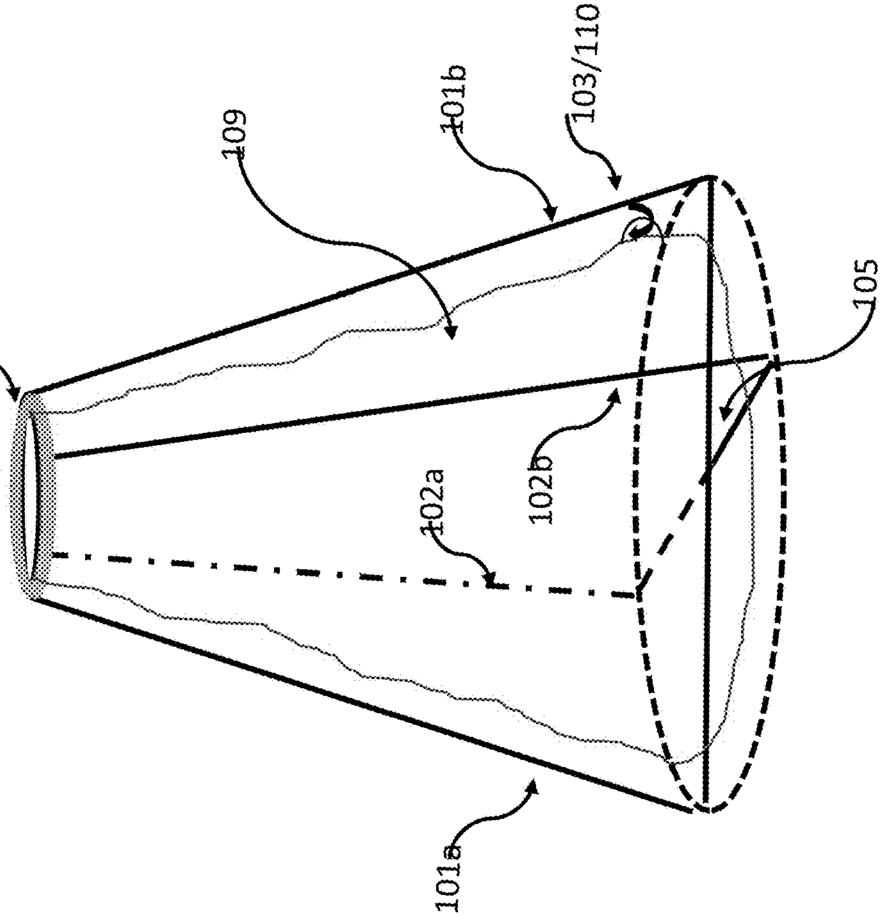

FIG. 3 A illustrates the conical support frame 100 including the rigid circular ring cap 106 attached to the gas permeable polymeric bag 109. The gas permeable polymeric bag 109 is attached to the upwardly extending distal ends 101*a* and 101*b* and 102*a* and 102*b* by the interconnection between hook 103 and rings 110 thereby extending and stabilizing the gas permeable polymeric bag 109 when being used, such as filling or during growth of any cell cultures.

FIG. 3 B show one of the most important aspect of the present invention, that being, the ability to remove the gas permeable polymeric bag 109 and the rigid circular ring cap 106 for folding of the conical support frame 100, wherein the upwardly extending distal ends 102*a* and 102*b* are moved on pivoting point 105 towards 101*b* and 101*a* to form a significantly flat configuration. Such foldability provides for easy storage. Notably, this FIG. 3B also shows another form of the conical support frame wherein the outside corners of the frame are curved. Such a curved corner 111 provides for easy fitting into flask clamp system commercially available to hold Erlenmeyer flask and provide stabilization during any shaking of the flask.

Figure 4:
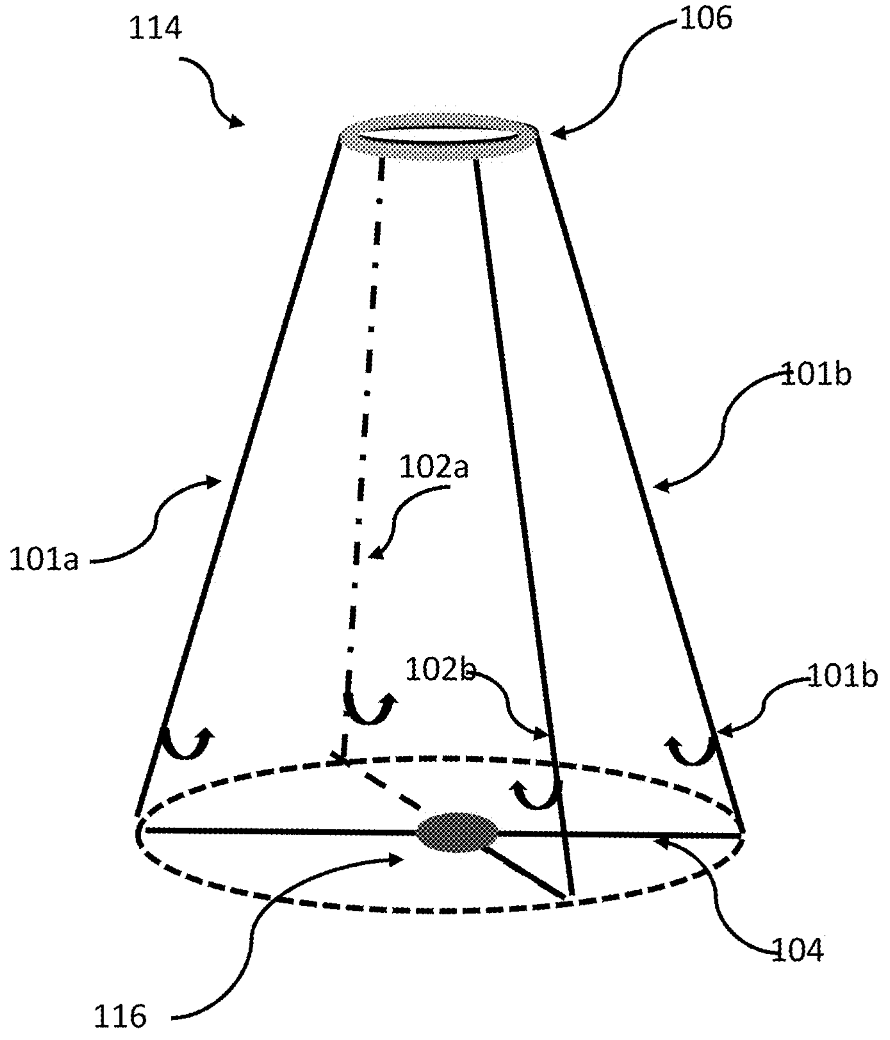
FIG. 4 illustrates a foldable support frame in an expanded configuration according to one embodiment of the invention.

FIG. 4 illustrates another embodiment showing conical support frame 114 including rod-type supports 101 and 102 each having proximal end forming a flat base and two opposing upwardly extending distal ends 101*a* and 101*b* and 102*a* and 102*b* to form a generally conical body, wherein the flat base 104 of the two rigid supports is split and connected at a central pivot point 116 thereby allowing the two rigid rod-type supports to form a conical body portion when separated furthest from each other. In this embodiment the flat sections of each rod-type support are split in the middle of the flat base section and individually inserted into a central pivoting central unit 116. This is different from the configuration of FIG. 1A where in rod 101 is position above rod 102 on a different horizontal plane. In contrast in the FIG. 4, the flat base of both rods 101 and 102 are positioned on the same horizontal plane. Again, this conical support frame 114 comprises a rigid circular ring cap 106 forming a tubular neck for placement and connecting thereto the upwardly extending distal ends 101*a* and 101*b* and 102*a* and 102*b* to stabilize the conical shaped frame.

Figure 5:
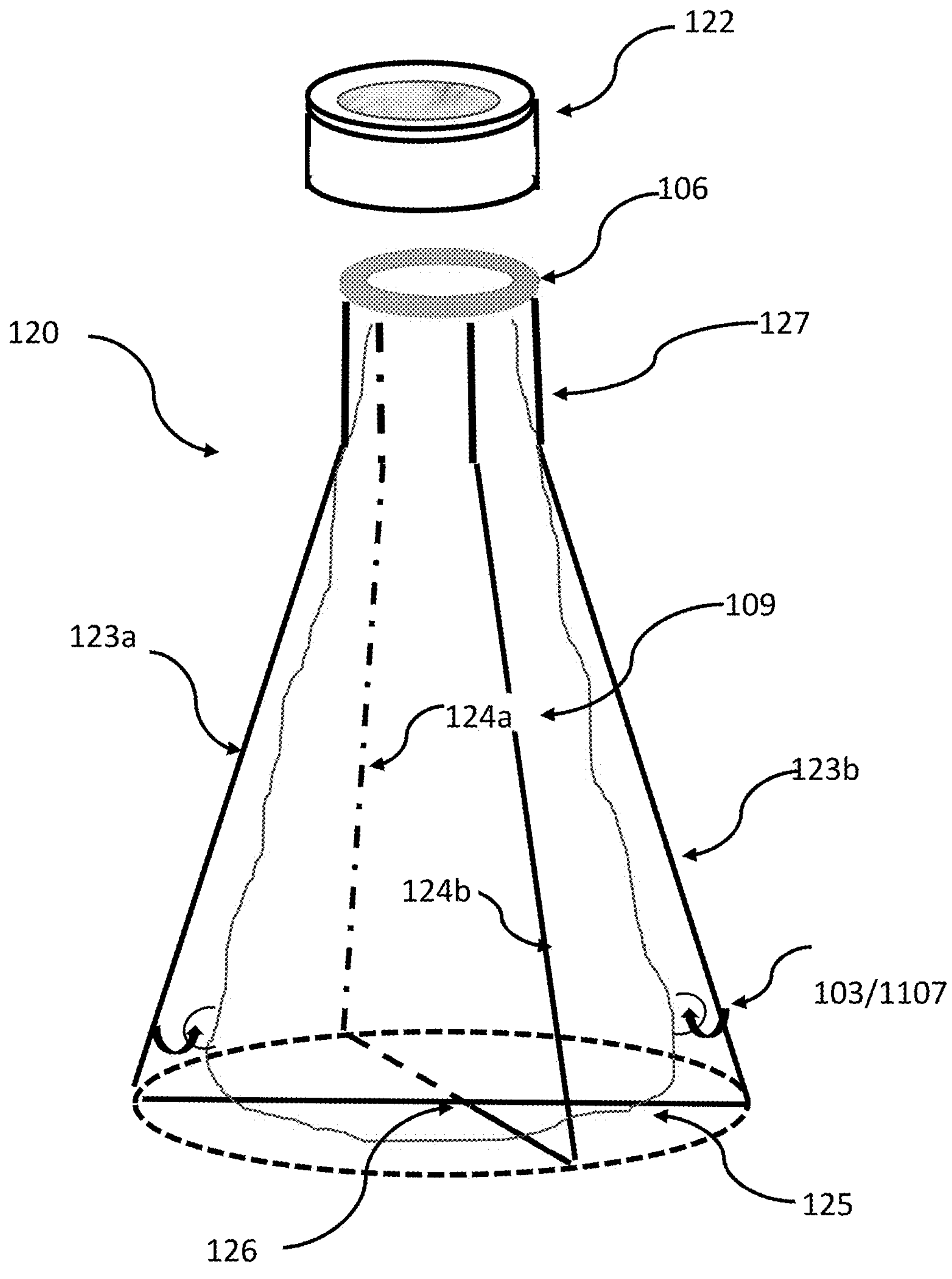
FIG. 5 illustrates a foldable support frame in an expanded configuration according to one embodiment of the invention and a rigid cap for connected to a neck section.

FIG. 5 illustrates another embodiment of a foldable Erlenmeyer shaped flask frame 120, in an expanded configuration which includes two rigid rod-type supports 123 and 124 each having proximal end forming a flat base and two opposing upwardly extending distal ends 123*a* and 123*b* and 124*a* and 124*b* to form a generally conical body, wherein the two rigid rod-type supports 123 and 124 extend vertically at an angle of about 150 to 170 degrees relative to the position of the 123 and 124 rods to form a tubular neck having a diameter less than the body portion, wherein the flat base 125 of the two rigid supports are connected at a central pivot point 125 thereby allowing the two rigid rod-type supports to form a conical body portion when separated furthest from each other. The Erlenmeyer shaped flask frame 120 further comprises a rigid circular ring cap 106 forming a tubular neck for placement and connecting thereto the upwardly extending distal ends 123*a* and 123*b* and 124*a* and 124*b* to stabilize the Erlenmeyer shaped flask frame. Included in the Erlenmeyer shaped flask frame is a non-rigid polymeric gas permeable bag 109 connected to the rigid circular ring cap 106. This embodiment further includes a stopper or a rigid screw type cap 122 for closure of the non-rigid gas permeable polymeric container or bag. The rigid screw type cap can further comprise a gas permeable section to provide removal of gases that rise to the top of the vessel such as carbon dioxide. For example, a silicone compound can be used for the gas permeable section to provide another section for diffusion of carbon dioxide from the interior of the bag.

The Erlenmeyer shaped flask frame 120 and circular cap 106 may be made from any rigid or substantially rigid polymeric materials described herein or otherwise suitable for such purposes, such as polyethylene (high-density or low-density polyethylene HDPE or LDPE), polyvinylchloride (PVC), polypropylene (PP), polystyrene (PS) including high impact polystyrene, polyamides (PA), acrylonitrile butadiene styrene (ABS), polycarbonate (PC), polycarbonate/acrylonitrile butadiene styrene (PC/ABS) etc.

Figure 6:
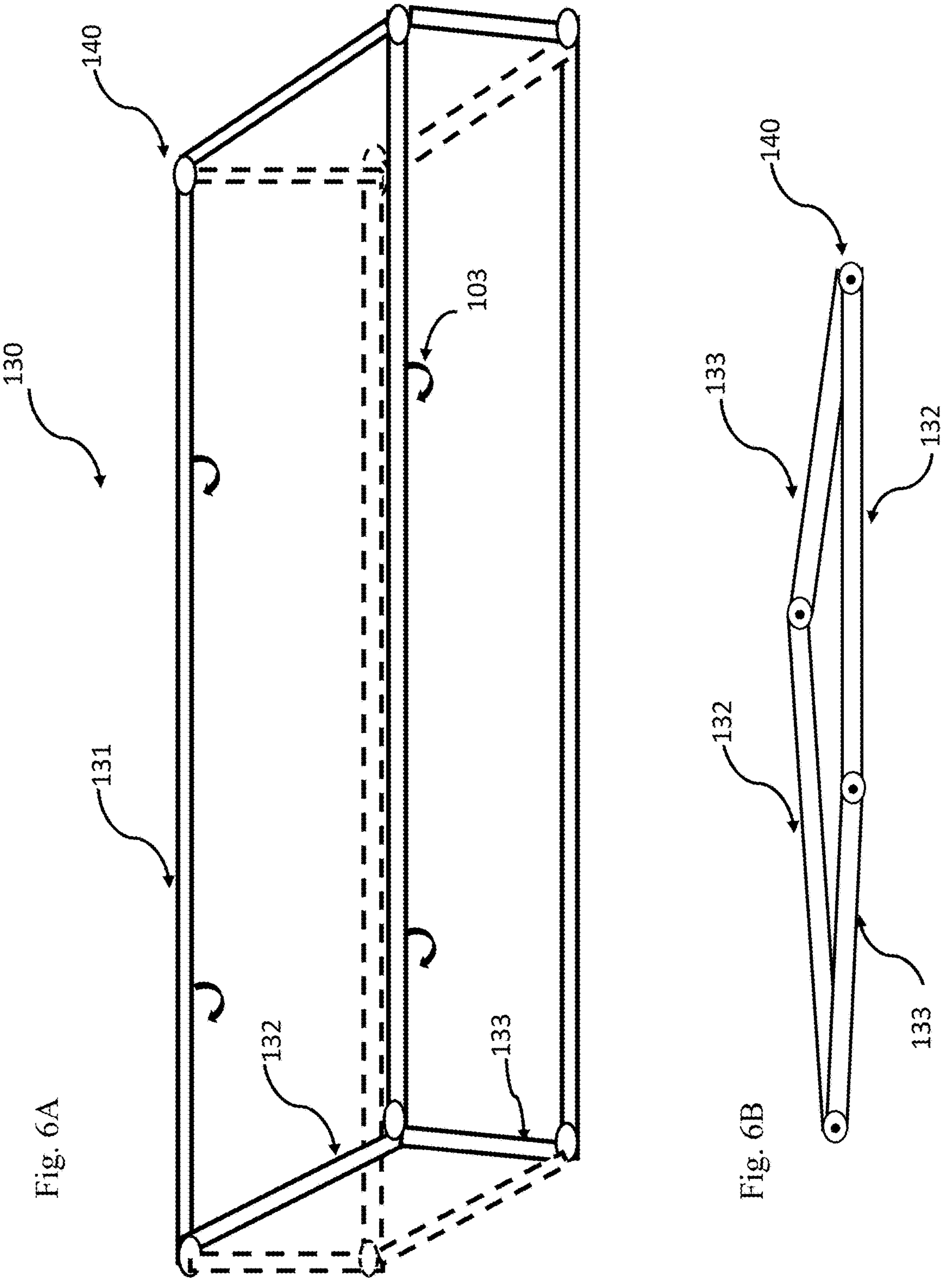
FIG. 6 A illustrates a three-dimensional support frame according to one embodiment of the invention.

The present invention also provides for a foldable and reusable T-flask frame as shown in FIG. 6. FIG. 6A illustrates a three-dimensional rectangular frame 130 comprised of four two dimensional rectangular frames each fabricated of four rods that form two dimensional rectangular frames, wherein two of the rectangular frames comprise to rods of 131 lengths perpendicularly attached to two rods of 132 length connected on all corners to a hinging mechanism 140 and two of the rectangular frames comprise to rods of 131 lengths perpendicularly attached to two rods of 133 length and connected on all corners to a hinging mechanism 140, wherein all the frames have the same longitudinal length of 131 rod and rods 132 have an increased length relative to the 133 rods. FIG. 6 B shows the folding position of the foldable T-flask.

Figure 7:
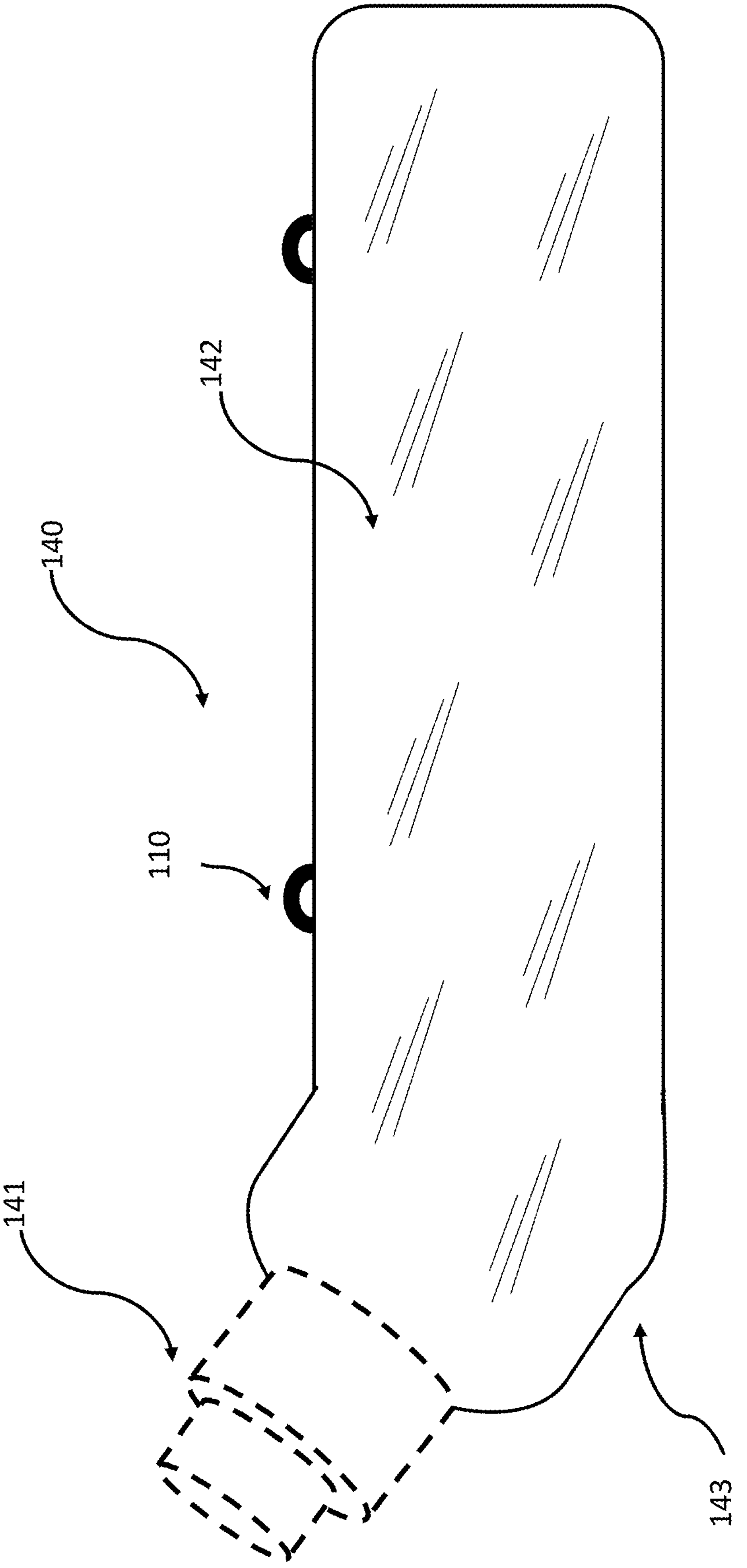
FIG. 7 illustrates an example of a collapsible bag in expanded configuration for inclusion in the support frame of FIG. 6 A.

FIG. 7 illustrates a gas permeable polymeric pouch or bag 140 for insertion into the T-flask frame, the expandable position, shown in FIG. 6A. The pouch or bag 140 has a longitudinal length 142 that fits with the framework of 130 and an angled extension 143 that include a closure cap 141. The angled extension provides for easily access for filing the pouch. Preferably the angled extension 143 is fabricated from a sturdy polymeric material communicatively connected to the gas permeable section 142. The pouch or bag can optionally include connecting rings 110 for connecting to 103 hooks shown in FIG. 6A. Several gas-permeable materials have gas permeability sufficient to permit free passage of oxygen and carbon dioxide and can be selected from a group including, but not limited to, silicone compounds such as polydimethylsiloxane (PDMS), poly1-trimethylsilyl-1-propyne (PMSP), polypropylmethylsiloxane, polytrifluoropropylmethylsiloxane, and polyphenylmethylsiloxane; fluoroethylenepolypropylene, polyolefin, ethylene vinyl acetate copolymer, polyethylene, a cellulose acetate, a methacrylate, a hybrid material or a phthalate. Preferably, a silicone compound is used to fabricate the pouch.

Figure 8:
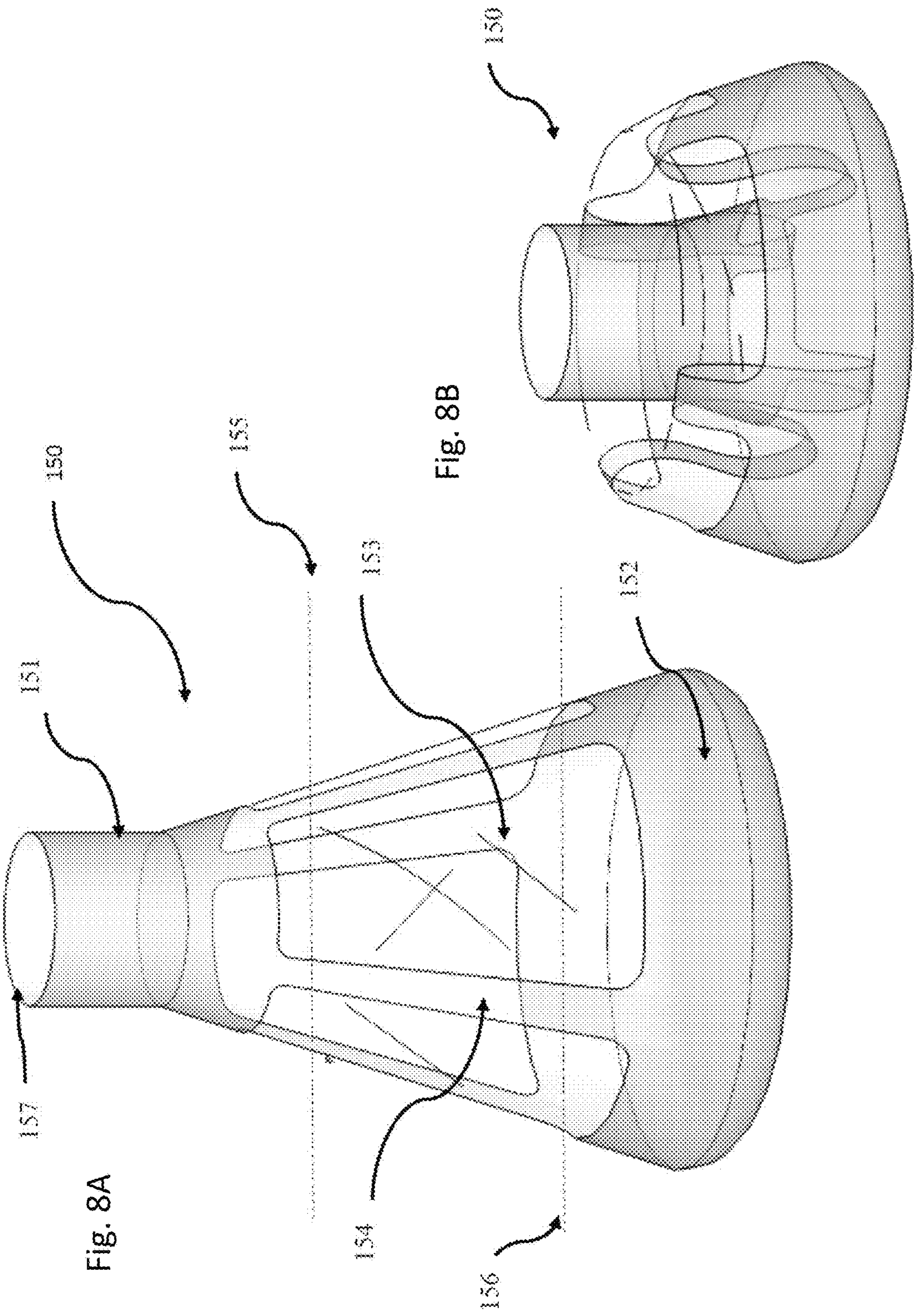
FIG. 8 A illustrates an example of a collapsible flask in an expanded configuration according to one embodiment of the invention.

FIG. 8 A illustrates a collapsible Erlenmeyer flask shaped vessel 150 fabricated of both a gas permeable and a non-gas permeable polymeric film comprising: a flat base 152, a generally conical body portion 153 and 154, a generally tubular neck 151 having a diameter less than the body portion and a mouth of the tubular neck 157 for moving fluid into and out of the vessel. The generally conical body portion comprises strips of connecting gas permeable 153 and non-gas permeable polymeric 154 sections, wherein the non-gas permeable sections provide sufficient support for maintaining the conical shape and the gas permeable polymeric sections cover a greater area from that of the non-gas permeable polymeric sections. Both the gas permeable and non-gas permeable polymeric films are sufficiently strong to maintain shape of the vessel and sufficiently flexible to allow collapsibility of the vessel. Optionally the tubular neck and mouth of the vessel may be provided with a rigid sealable cap. The tubular neck can include a threaded section to provide the option of using a screw on cap to provide sealable closure.

The collapsibility of the vessel shown in FIG. 8 B is effected by collapsing the top section, shown above the 155 section line, into the middle section, shown above the 156 section line, and both in the bottom section of the vessel when the vessel is in an upright position. Thus, the sections of the vessel are collapsed vertically to form a collapsed configuration. In the compressed or collapsed position, the vessel is in a better arrangement for storage or transport. The vessel can easily be opened into an expanded vessel by simply moving the top, and middle section away from the bottom section.

The gas permeable polymeric film provides adequate rates of carbon dioxide and oxygen permeability while preventing passage of liquid. Several gas-permeable materials used in 153 section have gas permeability sufficient to permit free passage of oxygen and carbon dioxide and can be selected from a group including, but not limited to, silicone, fluoroethylenepolypropylene, polyolefin, ethylene vinyl acetate copolymer, polyethylene, a cellulose acetate, a methacrylate, a hybrid material, or a phthalate. The non-gas permeable sections 154 can be any plastic commonly used in traditional culture vessels, or any other cell attachment material known to those skilled in the art.

Figures 9, 9A, 9B:
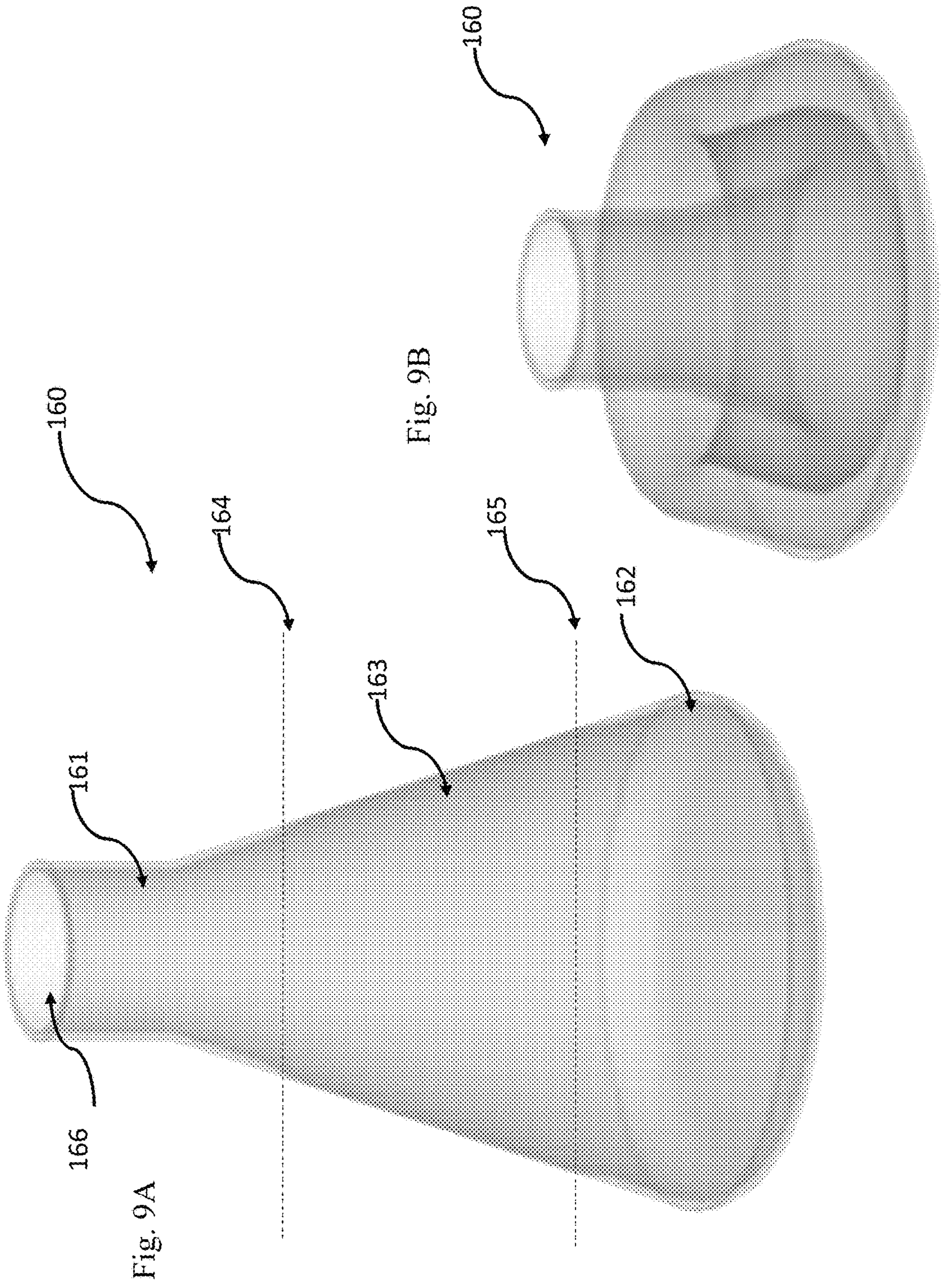
FIG. 9 A illustrates an example of a collapsible flask in an expanded configuration according to one embodiment of the invention.

FIG. 9 A illustrates a collapsible Erlenmeyer flask shaped vessel 160 fabricated of a gas permeable e polymeric film comprising: a flat base 162, a generally conical body portion 163, a generally tubular neck 161 having a diameter less than the body portion and a mouth of the tubular neck 166 for moving fluid into and out of the vessel. The collapsible Erlenmeyer flask shaped vessel is fabricated of gas permeable film that is sufficiently strong to maintain shape of the vessel and sufficiently flexible to allow collapsibility of the vessel. Optionally the tubular neck and mouth of the vessel may be provided with a rigid sealable cap. The tubular neck can include a threaded section to provide the option of using a screw on cap to provide sealable closure.

The collapsibility of the vessel shown in FIG. 9 B is effected by collapsing the top section, shown above the 164 section line, into the middle section, shown above the 165 section line, and both in the bottom section of the vessel when the vessel is in an upright position. Thus, the sections of the vessel are collapsed vertically to form a collapsed configuration. In the compressed or collapsed position, the vessel is in a better arrangement for storage or transport. The vessel can easily be opened into an expanded vessel by simply moving the top, and middle section away from the bottom section.

The gas permeable polymeric film provides adequate rates of carbon dioxide and oxygen permeability while preventing passage of liquid. Several gas-permeable materials used in the vessel 160 have gas permeability sufficient to permit free passage of oxygen and carbon dioxide and can be selected from a group including, but not limited to, silicone, fluoroethylenepolypropylene, polyolefin, ethylene vinyl acetate copolymer, a cellulose acetate, a methacrylate, or a phthalate.

Figure 10:
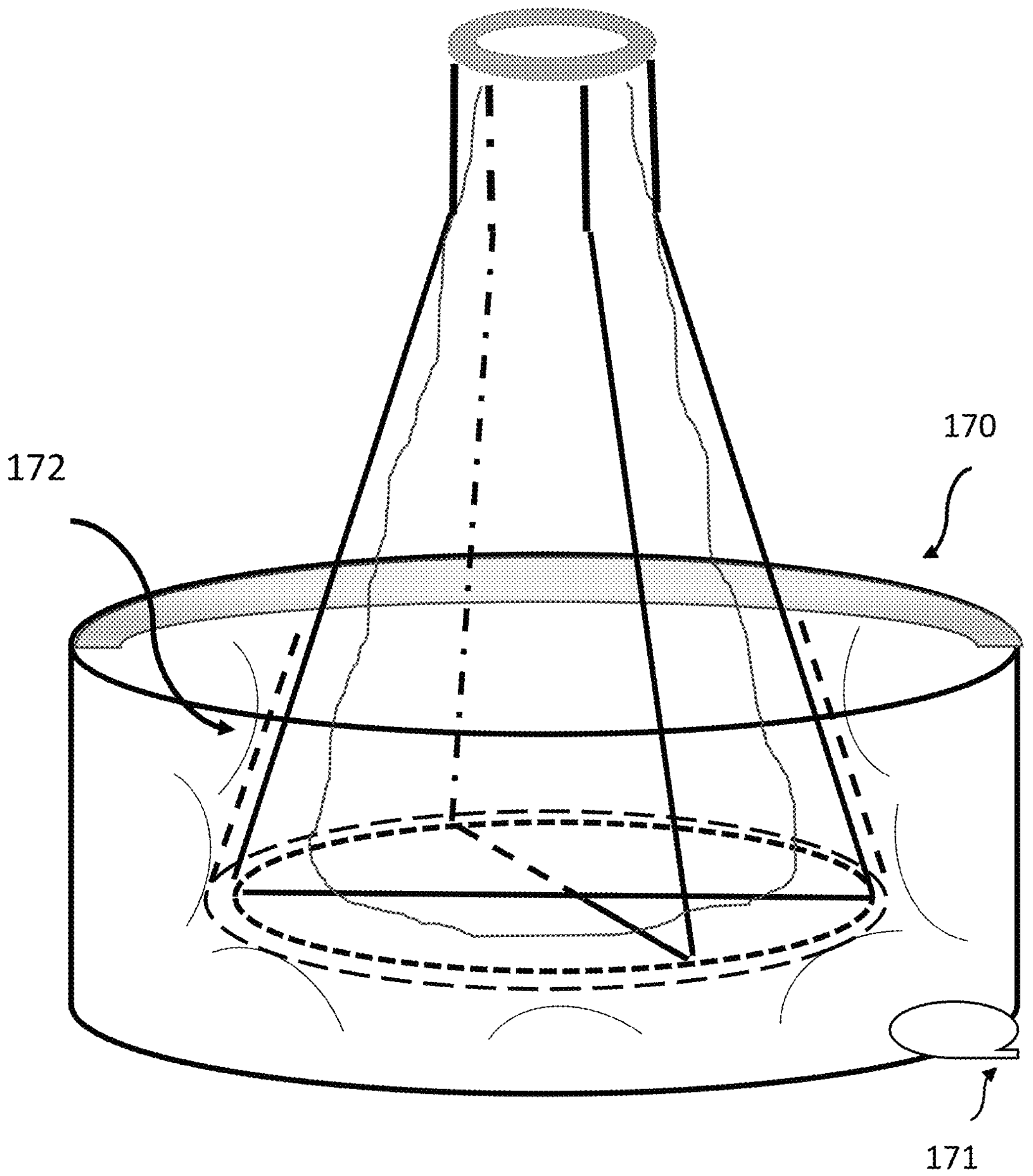
FIG. 10 illustrates an inflatable support holder for stabilizing a flask of the present invention.

FIG. 10 shows an inflatable support holder 170 for a flask of the present invention. Upon inflation, the holder surrounds the flask and provides support by inflating a rim 172 that surrounds the flask. The holder can be fabricated of polymeric material including but not limited to include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

The inflatable holder defines a collapsible, substantially fluid-tight container. The container is formed to have a reduced neck portion formed by the inflated rim 172, a flat bottom for stability and having a valve 171 therein for filling the support with air. The reduced neck fits around the flask body. The valve may comprise a stem extending outward from a side of the support and a removable plug for sealing the stem. Ordinarily, about 4 to 10 pounds per square inch of air is sufficient to properly inflate the structure.

Figure 11:
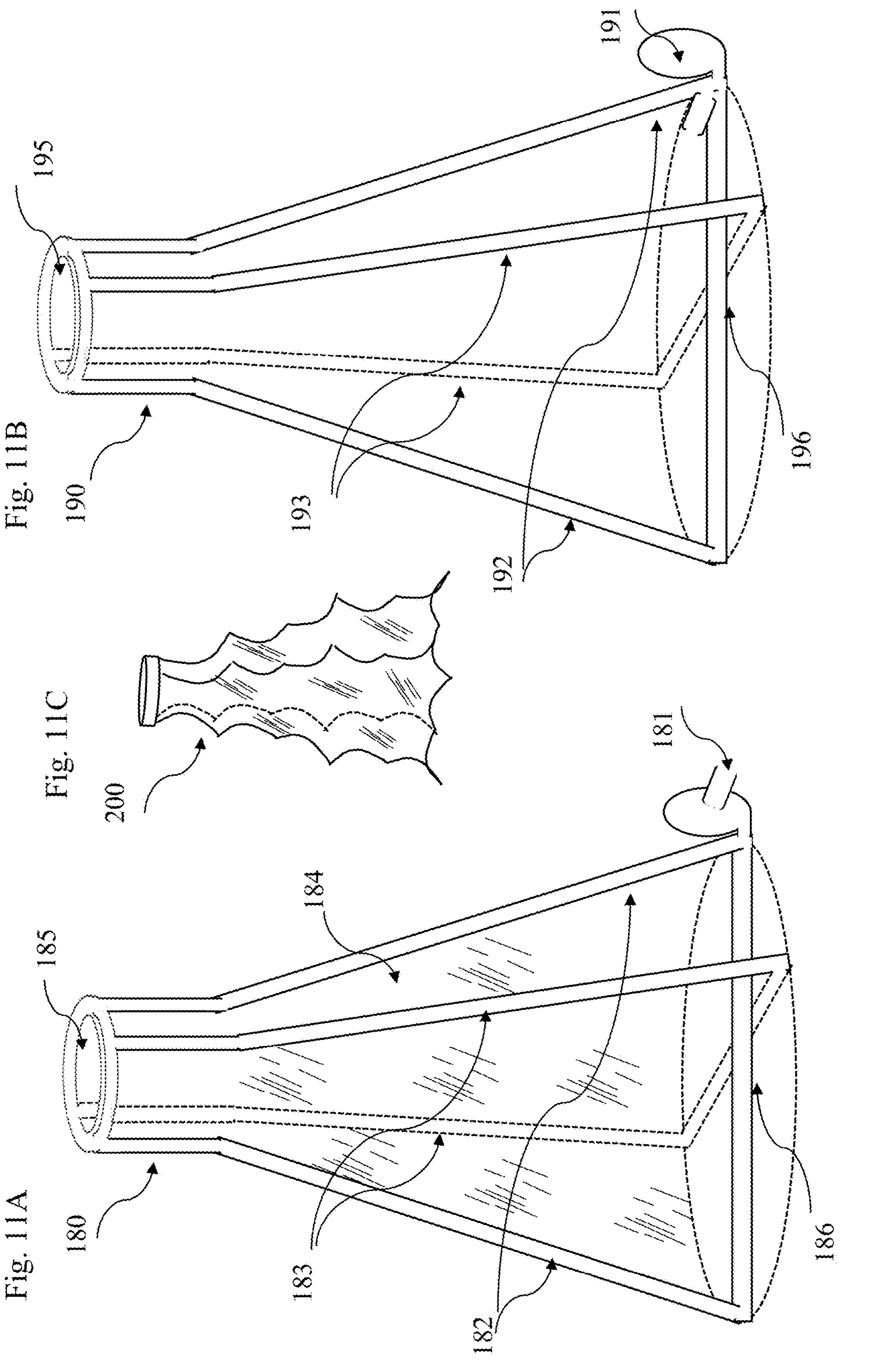
FIG. 11 A illustrates an inflatable flask with gas permeable inserts to hold a liquid, wherein gases escape from gas permeable inserts.

FIG. 11 A illustrates an inflatable flask structure 180 wherein the structures comprise a plurality of pneumatically interconnected, elongate inflatable tubes 182 and 183 positioned in spaced-apart relation to provide a conical shaped structure for being inflated in unison, said tubes defining a flask type structure have an opening ring structure 185 at the proximal end and flat bottom structure 186 at the distal end. Further included is a valve means 181 for inflating the tubes. Still further this embodiment comprises a plurality of wall panels 184 attached from and between adjacent tubes to define an enclosure of the flask, wherein the plurality of wall panels 184 are fabricated from a gas permeable polymeric material and wherein the inflatable tubes are fabricated from an impermeable and flexible polymeric material.

The inflatable tubes are preferably fabricated of a flexible gas impermeable material such as a rubberized material, polymeric material, or a thermoplastic sheet material, wherein the material has sufficient density to resist passage of air under pressure. When inflated the flask sharped structure is formed. Valve means 181 is provided for inflating the tubes, wherein the valve means includes a manifold into which all of the tubes interconnect and the tubes are connected with an air pump for inflation. Ordinarily, about 4 to 10 pounds per square inch of air is sufficient to properly inflate the structure and maintain the stability of the structure.

When air pressure is reduced the structure 200 collapses as shown in FIG. 11 C.

FIG. 11 B illustrates an inflatable flask structure 190 wherein the structures comprise a plurality of pneumatically interconnected, elongate inflatable tubes 192 and 193 positioned in spaced-apart relation to provide a conical shaped structure for being inflated in unison, said tubes defining a flask type structure have an opening ring structure 195 at the proximal end and flat bottom structure 196 at the distal end. Further included is a valve means 191 for inflating the tubes. The inflatable tubes are fabricated from a gas impermeable and flexible polymeric material.

The inflatable tubes are preferably fabricated of a flexible gas impermeable material such as a rubberized material, polymeric material, or a thermoplastic sheet material, wherein the material has sufficient density to resist passage of air under pressure. When inflated the flask sharped structure is formed. Valve means 191 is provided for inflating the tubes, wherein the valve means includes a manifold into which all of the tubes interconnect and the tubes are connected with an air pump for inflation. Ordinarily, about 4 to 10 pounds per square inch of air is sufficient to properly inflate the structure and maintain the stability of the structure.

Figure 12:
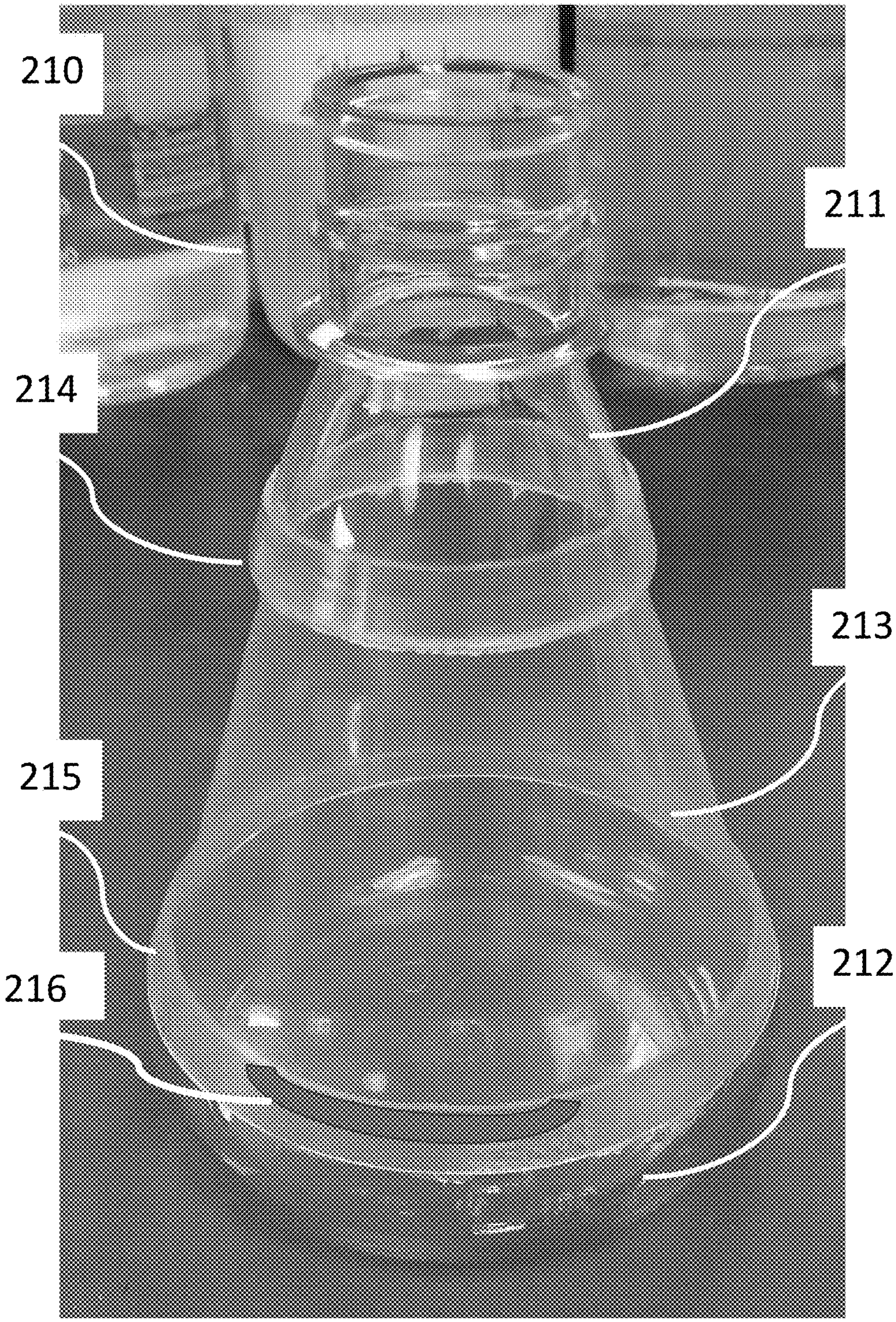
FIG. 12 illustrates a collapsible flask comprising three sections.
Figure 13:
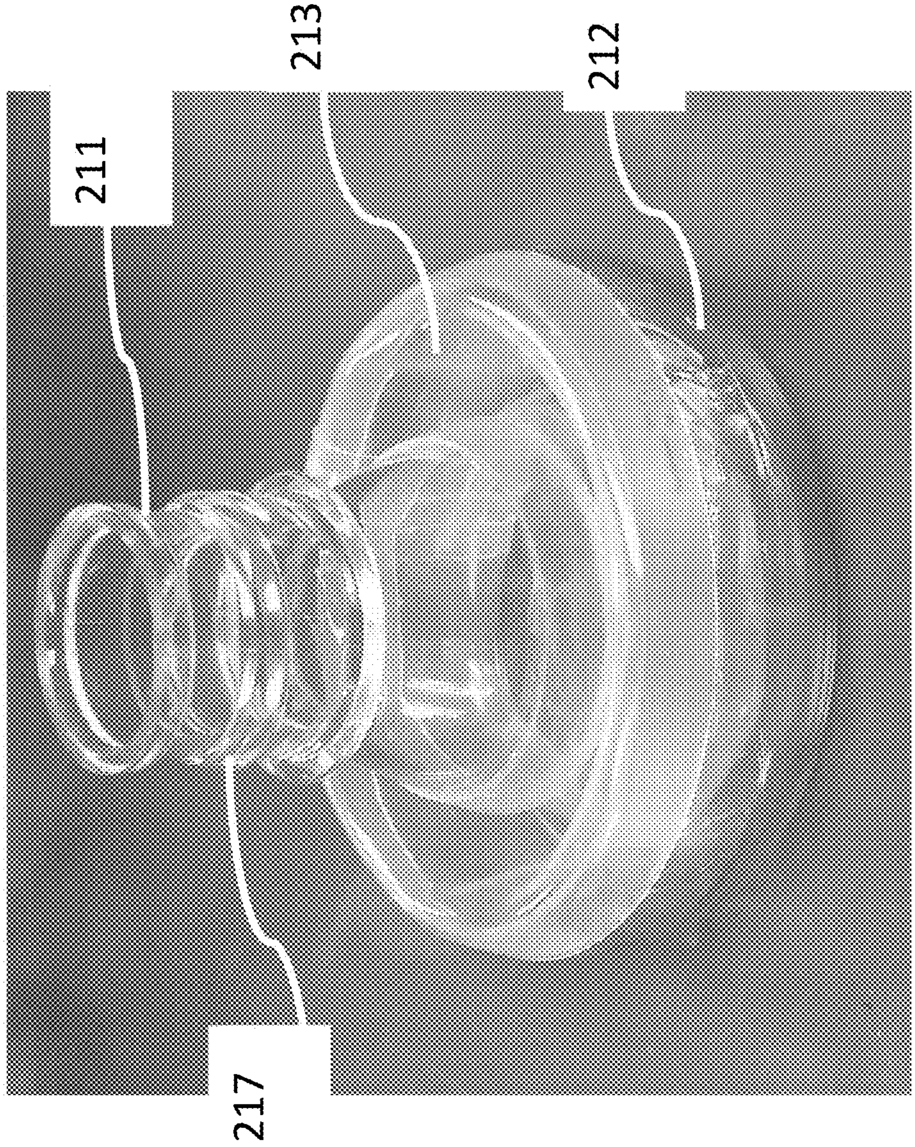
FIG. 13 illustrates the collapsible flask of FIG. 12 in a folded and collapsed position.

FIG. 12 illustrates another embodiment, providing a collapsible conical shaped Erlenmeyer flask 210 comprising three sections, wherein the first section is a non-flexible neck section 211, the second section comprises a non-flexible flat bottom bowl section 212 and a third section comprising a flexible sleeve 213 that is positioned between the first and second section and connected to each to form a sealed collapsible Erlenmeyer flask, wherein the flexible sleeve 213 collapsibly folds upon itself to position the non-flexible neck section 211 closer to the non-flexible flat bottom bowl section 212, as shown in FIG. 13. In the folding process, the neck section and substantially all of the flexible sleeves are contained with the non-flexible flat bottom bowl section, thereby reducing the size for easy storage.

The flexible sleeve comprises a first opening having smaller cross-section diameter than a second opening, wherein the first and second opening are positioned at opposite ends of the flexible sleeve and where in the first opening is connect to the non-flexible neck section at 214 and the second opening is connected to the non-flexible flat bottom bowl section 215. The flexible sleeve is connected to both the non-flexible neck section and the non-flexible flat bottom bowl section by meeting the edges of each and overlapping a bottom section of the non-flexible neck section 214 and the top section of the non-flexible flat bottom bowl section 215. The flexible sleeve has the ability and elasticity to stretch over the bottom edge of the neck section and the top edge of the non-flexible flat bottom bowl section. Additionally, a sealing band can be connected to flexible sleeve at the junction point of the overlapping sleeve section to the neck section and flat bottom bowl section. The sealing bands may be a narrow metal strip 216 wherein the bands can be slipped over the neck section for positioning at the appropriate junction points. In FIG. 12, the sealing band is shown in a truncated form just to provide preferred positioning.

The non-flexible material used to fabricate the neck section and flat-bottom bowl section can be selected from glass or a polymer, and preferably transparent. A hard nonflexible polymer includes but is not limited to High-density polyethylene(HDPE), Polypropylene (PP), Polycarbonate, Polyvinyl chloride (PVC), Polystyrene (PS), Nylon, nylon 6, nylon 6,6, Teflon (Polytetrafluoroethylene) and Thermoplastic polyurethanes (TPU). Preferably the non-flexible and hard material is heat resistant.

The flexible polymeric material acceptable to fabricate the flexible sleeve may include any flexible gas permeable film, such as discussed above and preferably a silicone material.

The neck section 211 is preferably configured to include a top and bottom section 214 where the top section is threaded 217 to provide the ability to connect a screw type cap to enclose the collapsible conical shaped Erlenmeyer flask. The neck section can include a threaded section to provide the option of using a screw on cap to provide sealable closure.

The flexible sleeve 213 is conical shaped wherein the first opening is of sufficient diameter to overlap the bottom edge of the neck section 214 and the second opening opposite the first opening has a larger diameter than the first opening is of sufficient diameter to overlap the top edge of the flat-bottom bowel section. 215. Notably the first and second opening are position on a plane that is perpendicular to the longitudinal axis of the flexible sleeve.

Testing of Gas Permeability of Silicon Containing Collapsible Flasks

Shake flasks are ubiquitous in fermentation, however, there is typically a paucity of oxygen along with carbon dioxide buildup during cell growth in a shake flask. This is due to insufficient gas transfer between the environment and flask during aerobic growth. The present invention provides plastic shake flasks with gas permeable silicone membrane walls with portable, non-collapsible and collapsible designs. The silicone walls allow for improved transfer of oxygen and carbon dioxide to and from the environment increasing availability of oxygen for cell growth while minimizing carbon dioxide buildup. *E. coli* fermentations were conducted in both commercial standard shake flasks and modified gas permeable flasks. The important factors that affect cell growth, namely dissolved oxygen and dissolved carbon dioxide were measured using noninvasive sensors, and cell growth was compared.

Materials and Methods

For these experiments, a noninvasive method of measuring dissolved oxygen (DO) was used wherein such a method included using an optical sensor. The oxygen sensitive component was a thin film attached to the bottom of the flask which responds differently to light of certain wavelengths at different dissolved oxygen concentrations. The device had been tested to be accurate up to 60% dissolved oxygen concentration in previous studies conducted by the inventors. For dissolved carbon dioxide ($DCO_2$), a silicone sampling loop was inserted into the flask and then flushed with ambient air until the prior carbon dioxide in the loop was completely expelled. This was done after each measurement. The gas dissolved in the solution was then allowed to recirculate through the gas permeable silicone membrane into the sensor. The silicone tubing had a small spring within that prevented sharp folds and kinks and was also enclosed by a bigger spring to ensure that it hugged the walls of the shake flask and stayed in place at the bottom during trials. All trials were conducted for 24 hours at a temperature of 30° C. at 250 rpm in an incubator with a Lysogeny broth (LB) medium at a total volume of 150 ml. 40 standardized batches of 300 μl *E. coli* samples were first prepared and then frozen in 1 ml plastic containers of which 250 μl was used for each trial. They were thawed each time a trial was run; this was done to eliminate variability between *E. coli* samples by ensuring that each sample had been frozen and thawed exactly one time before being used in the trial. 250 μl of Ampicillin—a beta lactam antibiotic—was also used to ensure that all the *E. coli* in the sample was uniform and of the same kind. Silicone films of two thicknesses were studied—0.3 and 0.1 mm. Silicone epoxy was used to bind the silicone to the plastic shake flask and left to cure for 24 hours. Distilled water (DI) was then introduced into the flask to check for leakages, which if present, were plugged with more silicone epoxy. Testing on the 0.1 mm thickness silicone was conducted without autoclaving to ensure stability of the film.

Figure 14:
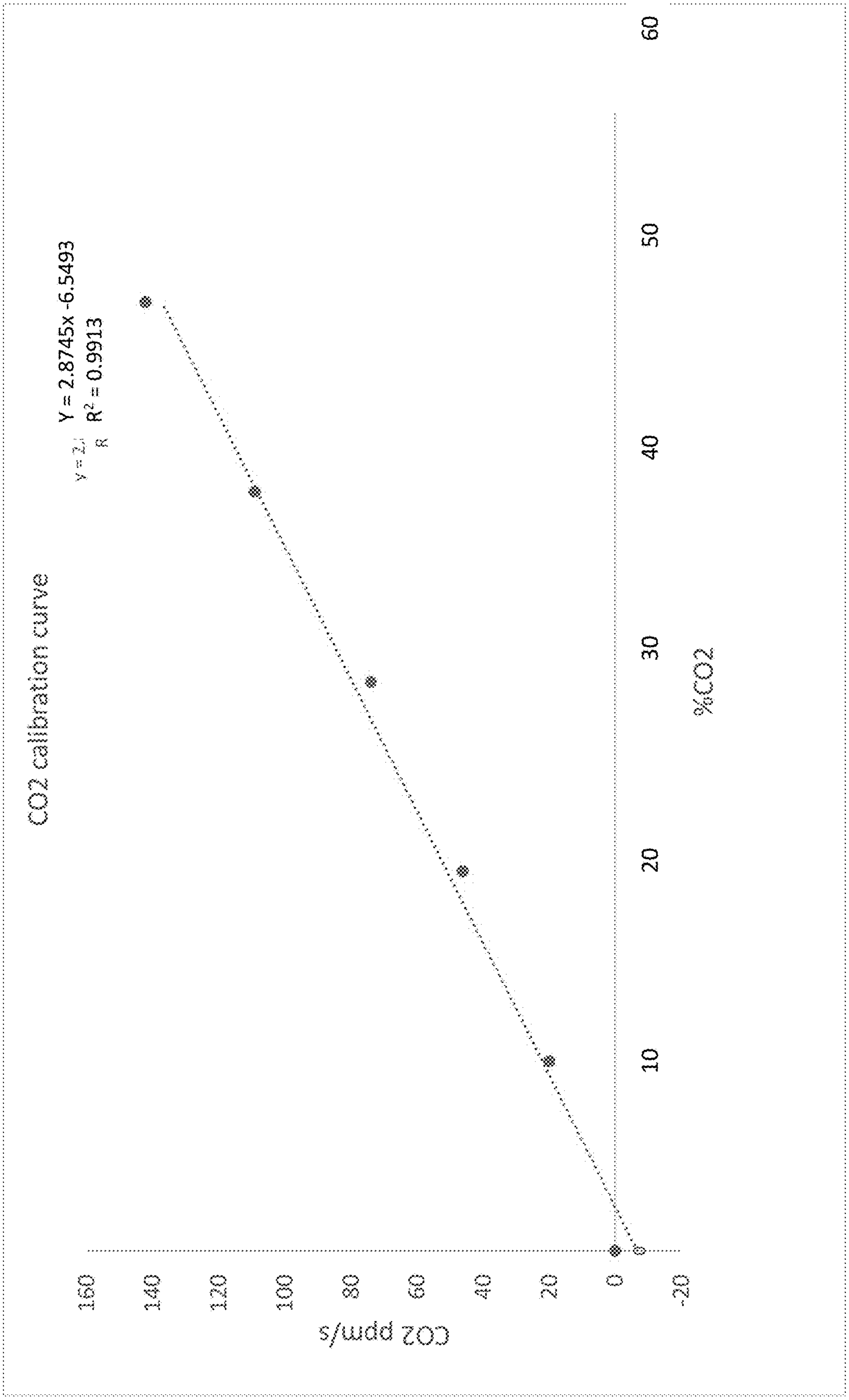
FIG. 14 shows the calibration curve for $DCO_2$ probes.

Carbon dioxide was calibrated using known concentrations of $CO_2$ gas. FIG. 14 is an example of a $CO_2$ calibration curve where the y-axis is the slope of the $CO_2$ sampling curve (ppm vs time) and the x-axis is the known gas percentage of $CO_2$ passed through a reference LB broth solution.

Figure 15:
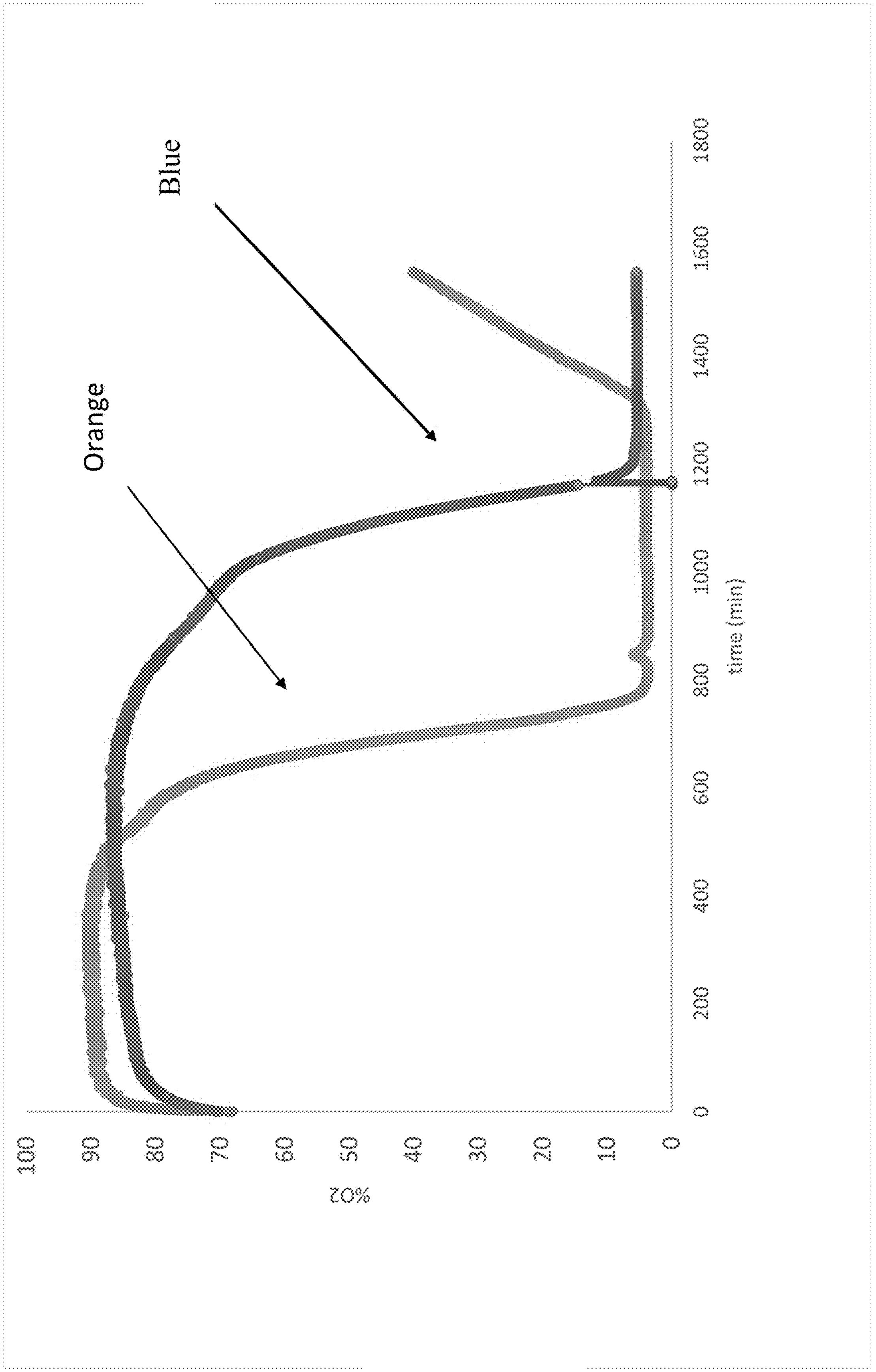
FIG. 15 DO curve for 0.3 mm silicone thickness (blue) and solid walled (orange) shake flask variants for *E. coli* growth in LB broth.

It was noticed that using compressible silicone walls of 0.3 mm sped up the rate of oxygen consumption and by extension, *E. coli* growth and demonstrated an increased availability of oxygen after the growth phase as compared to the polymer flask, as shown in FIG. 15. Of the two silicone film thicknesses studied—0.3 and 0.1 mm—it was hypothesized that the 0.1 mm film would provide greater gas permeability than the 0.3 mm.

Figure 16:
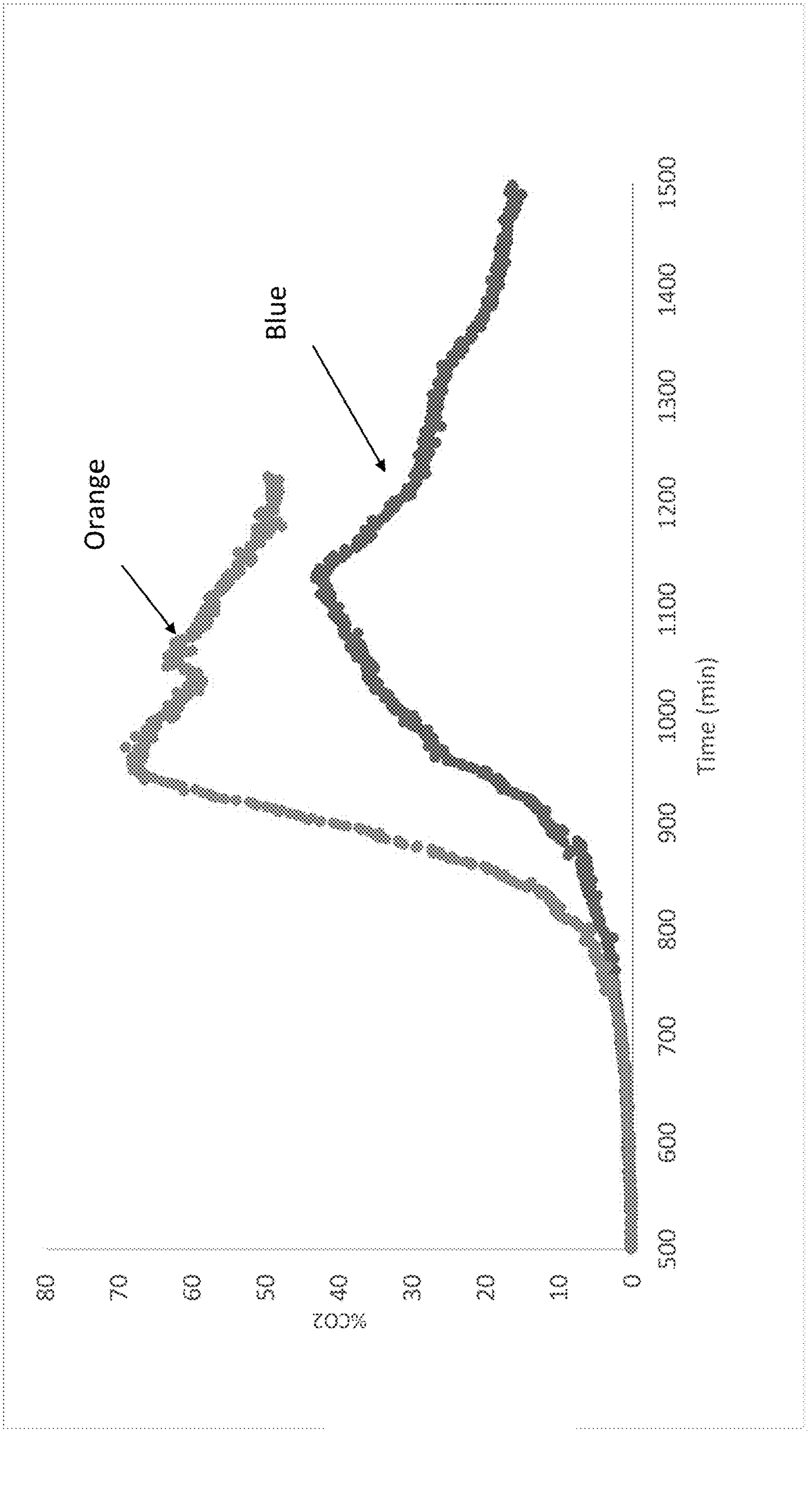
FIG. 16 $DCO_2$ curve for 0.3 mm silicone thickness (blue) and solid walled (orange) shake flask variants for *E. coli* growth in LB broth.

Dissolved carbon dioxide ($DCO_2$) also followed the expected trend where the no silicone plastic shake flask had a higher concentration of $DCO_2$ than the silicone walled variant as shown in FIG. 16.

The results show that the oxygen limitation usually occurring in standard shake flasks was significantly improved in the modified shake flasks with a silicone section and cell growth was similarly enhanced. There was an increase in available DO and a reduction in $DCO_2$ with 0.3 mm gas permeable silicone walls as opposed to plane plastic walls. As 0.1 mm silicone is thinner and more permeable than the 0.3 mm variant, it can be hypothesized that there would be greater available DO and lesser $DCO_2$.

Figure 17:
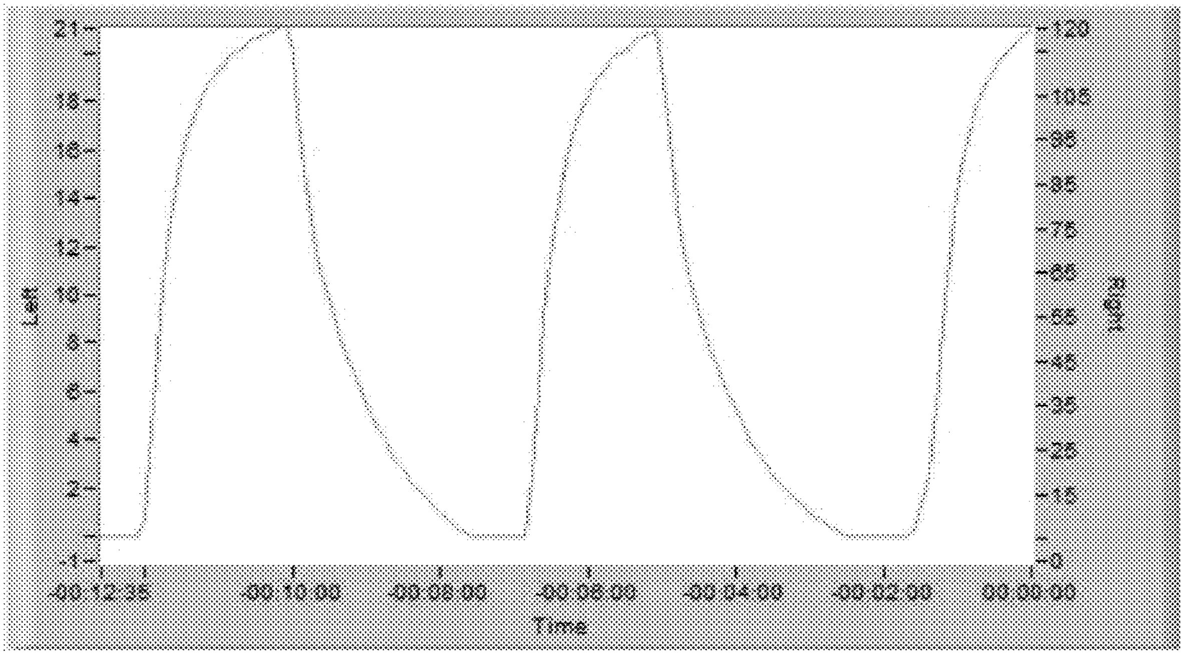
FIG. 17 shows the integrated oxygen sensor response curve with oxygen sensitive Ruthenium dye in silicone.
Figure 18A:
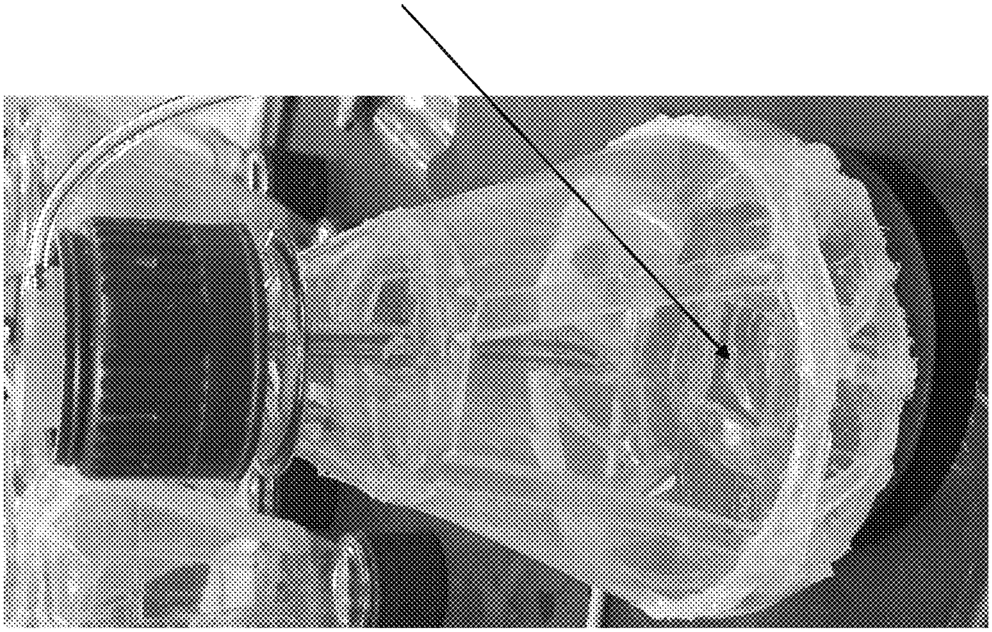
FIGS. 18 A and B shows a sensor spot using oxygen sensitive Ruthenium dye dissolved into silicone material (arrow) positioned on the bottom of the flask and made into the presently describes flasks of the present invention.
Figure 18B:
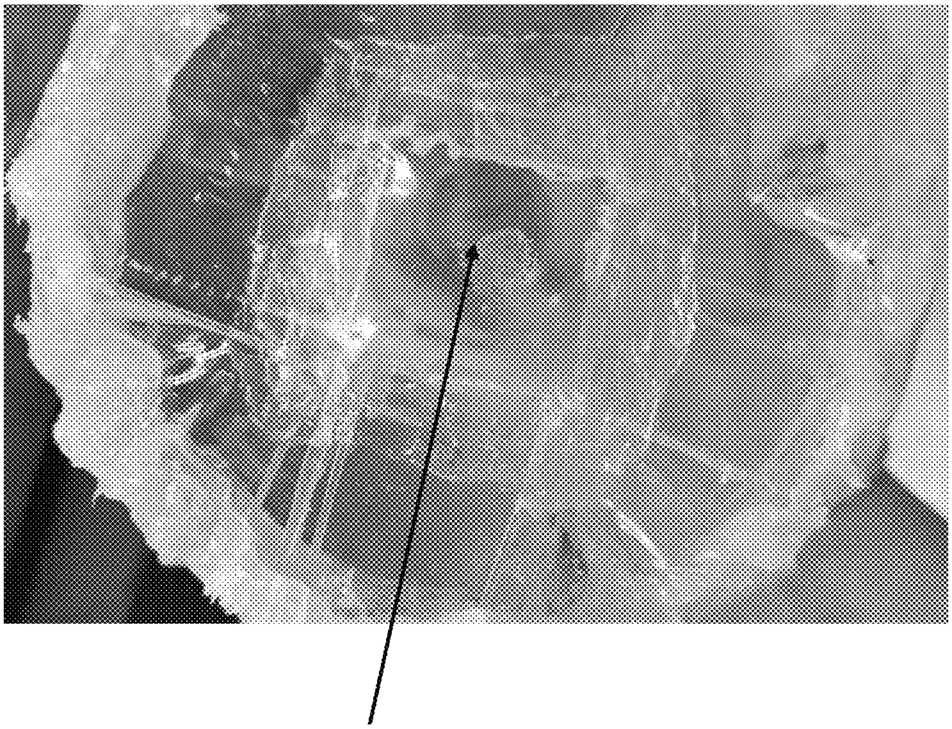
Figure 19:
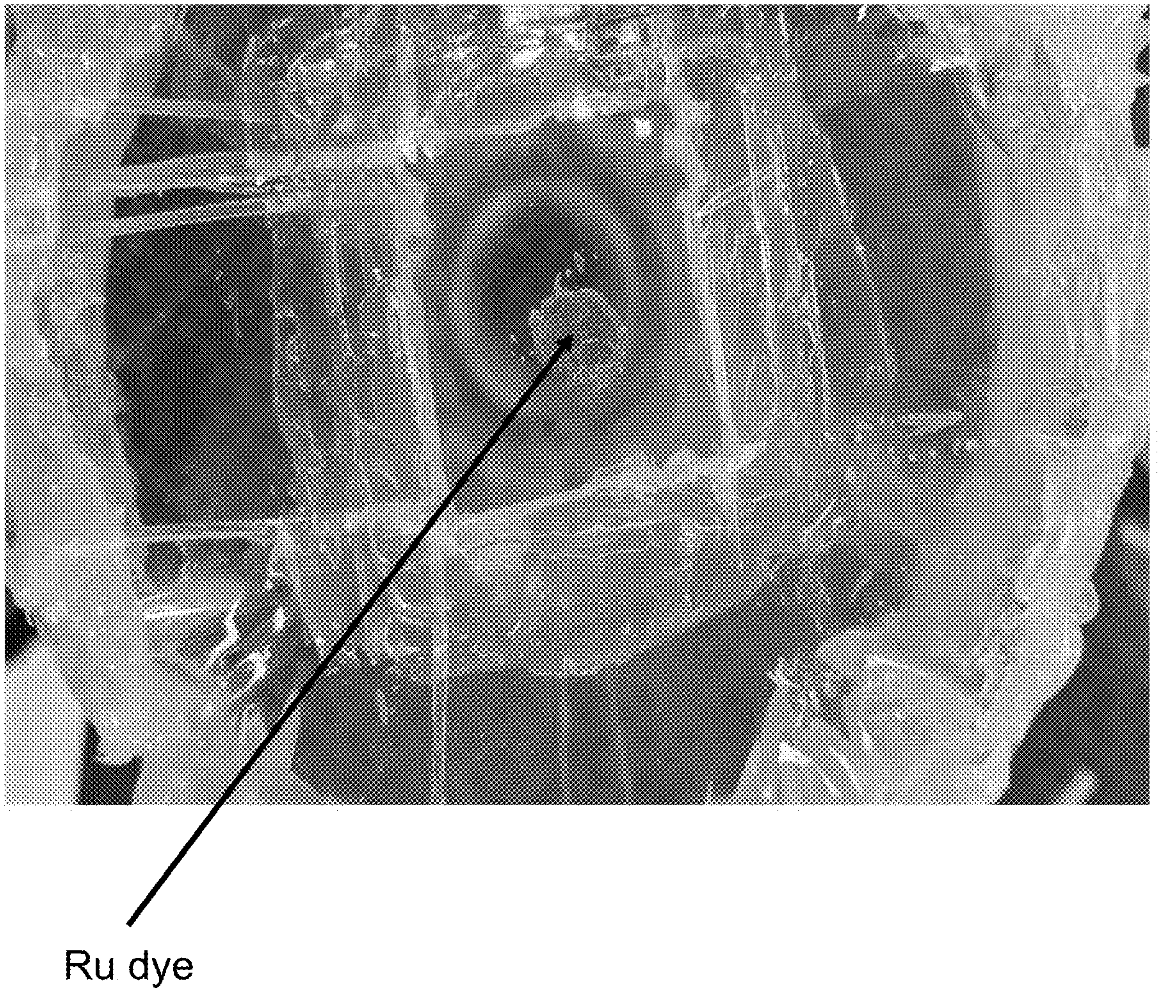
FIG. 19 shows an enlarged view of the FIG. 18 B with Ruthenium dye dissolved into silicone material (arrow).
Figure 20:
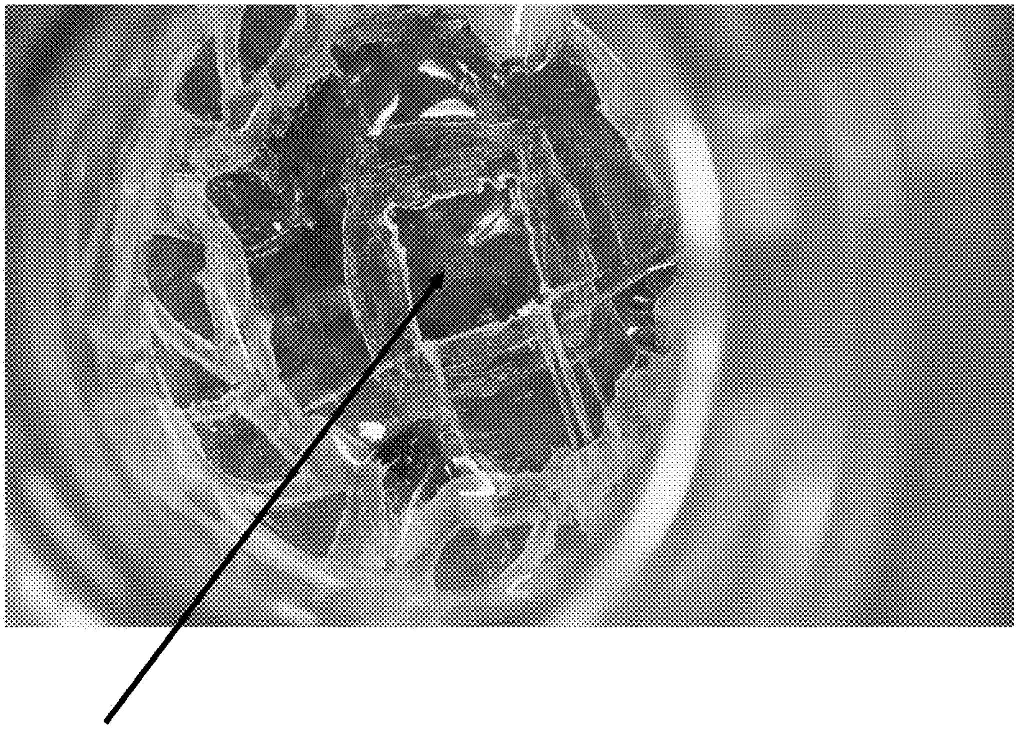
FIG. 20 shows another view of Ruthenium dye dissolved into silicone material (arrow) from the top of the flask.

FIG. 17 shows the results of oxygen interaction with the impregnated analyte sensor in the T-flask of the present invention. Specifically, The sensor spot shown in FIGS. 18, 19 and 20 was made by dissolving oxygen sensitive Ruthenium dye into silicone, which was then integrated with the silicone membrane structure of the flask. The outer later was sealed with protective plastic so that only oxygen from the flask side could affect the sensor.

That which is claimed is:

1. A conical shaped flask comprising:

a conical shaped frame comprised of two supports, wherein each of the two supports are approximately identical and each have a proximal end forming a flat base and two opposing upwardly extending distal ends forming a generally conical body, wherein the flat bases of the two supports are connected at a central pivot point thereby allowing the two supports to form a conical body portion when separated furthest from each other and foldable into an essentially flat frame when adjacent;

a rigid circular ring cap forming a tubular neck for placement and removably connecting thereto the upwardly extending distal ends of the two supports to stabilize the conical shaped frame, wherein the rigid circular ring cap has an exterior and interior edge; and a non-rigid gas permeable polymeric container or bag fabricated of a gas permeable polymeric material and sized to fit within the conical body portion and attached to the interior edge of the circular ring cap for positioning therein.

2. The conical shaped flask according to claim 1, wherein the rigid circular ring cap comprises four recesses/slots equally distributed within the bottom of the circular ring cap thereby providing connection to the upwardly extending distal ends.

3. The conical shaped flask according to claim 1, wherein the two supports comprise hooking attachments for securing the non-rigid gas permeable polymeric container or bag to the conical body portion.

4. The conical shaped flask according to claim 1, further comprising a top stopper or a rigid screw cap for closure of the non-rigid gas permeable polymeric container or bag.

5. The conical shaped flask according to claim 1, wherein the rigid circular ring cap is a cylindrical ring having a height thereby forming a neck wherein the neck has a uniform internal diameter for its entire height.

6. The conical shaped flask according to claim 1, wherein the gas permeable polymeric material is selected from the group consisting of silicone, polydimethylsiloxane (PDMS), poly1-trimethylsilyl-1-propyne (PMSP), polypropylmethylsiloxane, polytrifluoropropylmethylsiloxane, polyphenylmethylsiloxane, fluoroethylenepolypropylene, polyolefin, ethylene vinyl acetate copolymer, polyethylene, a cellulose acetate, a methacrylate, a hybrid material, and a phthalate.

7. The conical shaped flask according to claim 1, wherein the two supports are fabricated of a rigid material or substantially rigid material including a polymer or metal.

8. The conical shaped flask according to claim 6, wherein the gas permeable polymeric material further comprises an analyte or pH sensing material integrated or impregnated into at least one section of the non-rigid gas permeable polymeric container or bag to measure an analyte in a solution in or escaping from the non-rigid gas permeable polymeric container or bag.

9. The conical shaped flask according to claim 8, wherein the analyte is oxygen, nitrogen, glucose, glutamine, carbon dioxide, or ammonia.

* * * * *